United States Patent
Sackner et al.

[11] Patent Number: 6,155,976
[45] Date of Patent: Dec. 5, 2000

[54] RECIPROCATING MOVEMENT PLATFORM FOR SHIFTING SUBJECT TO AND FRO IN HEADWARDS-FOOTWARDS DIRECTION

[75] Inventors: Marvin A. Sackner, Miami Beach; D. Michael Inman, Miami, both of Fla.; William J. Meichner, Royal Oak, Md.

[73] Assignee: Nims, Inc., Miami Beach, Fla.

[21] Appl. No.: 09/317,571

[22] Filed: May 24, 1999

Related U.S. Application Data

[63] Continuation-in-part of application No. 09/041,578, Mar. 13, 1998, abandoned.
[60] Provisional application No. 60/040,457, Mar. 14, 1997, and provisional application No. 60/064,541, Nov. 5, 1997.

[51] Int. Cl.[7] .............................. A61B 5/00; A61G 7/00
[52] U.S. Cl. ................................. 600/300; 5/600
[58] Field of Search .................... 600/300, 323, 600/481, 529; 606/242, 245; 482/142, 143, 144; 5/607, 608, 609, 610, 905, 929, 600

[56] References Cited

U.S. PATENT DOCUMENTS

| | | |
|---|---|---|
| 1,733,115 | 10/1929 | Capito . |
| 2,512,621 | 6/1950 | Emerson ................................. 188/33 |
| 3,802,003 | 4/1974 | Laureti ...................................... 5/108 |
| 4,088,124 | 5/1978 | Korner et al. . |
| 4,258,446 | 3/1981 | McAllister et al. ....................... 5/109 |
| 4,586,492 | 5/1986 | Manahan ................................... 5/608 |
| 4,590,631 | 5/1986 | Varney ...................................... 5/101 |
| 4,619,270 | 10/1986 | Margolis et al. . |
| 4,730,064 | 3/1988 | Boggs . |
| 4,761,000 | 8/1988 | Fisher et al. .......................... 269/323 |
| 4,785,797 | 11/1988 | Cuervo . |
| 4,793,010 | 12/1988 | Gross et al. ............................... 5/109 |
| 4,934,997 | 6/1990 | Skakas ....................................... 5/107 |
| 4,970,740 | 11/1990 | Crawford ................................... 5/109 |
| 5,183,457 | 2/1993 | Gatts et al. .............................. 600/21 |
| 5,303,433 | 4/1994 | Jang .......................................... 5/109 |
| 5,423,862 | 6/1995 | Clarke et al. ............................. 5/608 |
| 5,442,710 | 8/1995 | Komatsu .................................. 381/24 |
| 5,520,614 | 5/1996 | McNamara et al. ..................... 601/24 |
| 5,555,891 | 9/1996 | Eisenfeld . |
| 5,572,903 | 11/1996 | Lee .......................................... 74/44 |
| 5,588,425 | 12/1996 | Sackner et al. . |

OTHER PUBLICATIONS

D.J. Bohn et al., "Ventilation by High–Frequency Oscillation", 1980, 710–716.

*Primary Examiner*—Eric F. Winakur
*Attorney, Agent, or Firm*—Cohen, Pontani, Lieberman & Pavane

[57] ABSTRACT

A reciprocating platform assembly for oscillating a subject supporting platform in a back and forth, headward to footward motion includes a platform mounted on displacement modules that are mounted to a frame. The displacement modules are signally connected to a processor that controls movement of the platform through operation of the displacement modules. The platform may be oscillated to soothe a subject on the platform to hasten a sleeping state of the subject or to minimize or prevent the occurrence of apneas in the subject. The platform may also be oscillated to assist or support ventilation and/or for cardiopulmonary/cardiac support of the subject. The platform is additionally useful in conjunction with a physiological monitor to rapidly shake the subject when an adverse event occurs to wake the subject and terminate the adverse event. The monitor may also be employed as a trigger for assisting or supporting ventilation and cardiac/cardiopulmonary support.

78 Claims, 22 Drawing Sheets

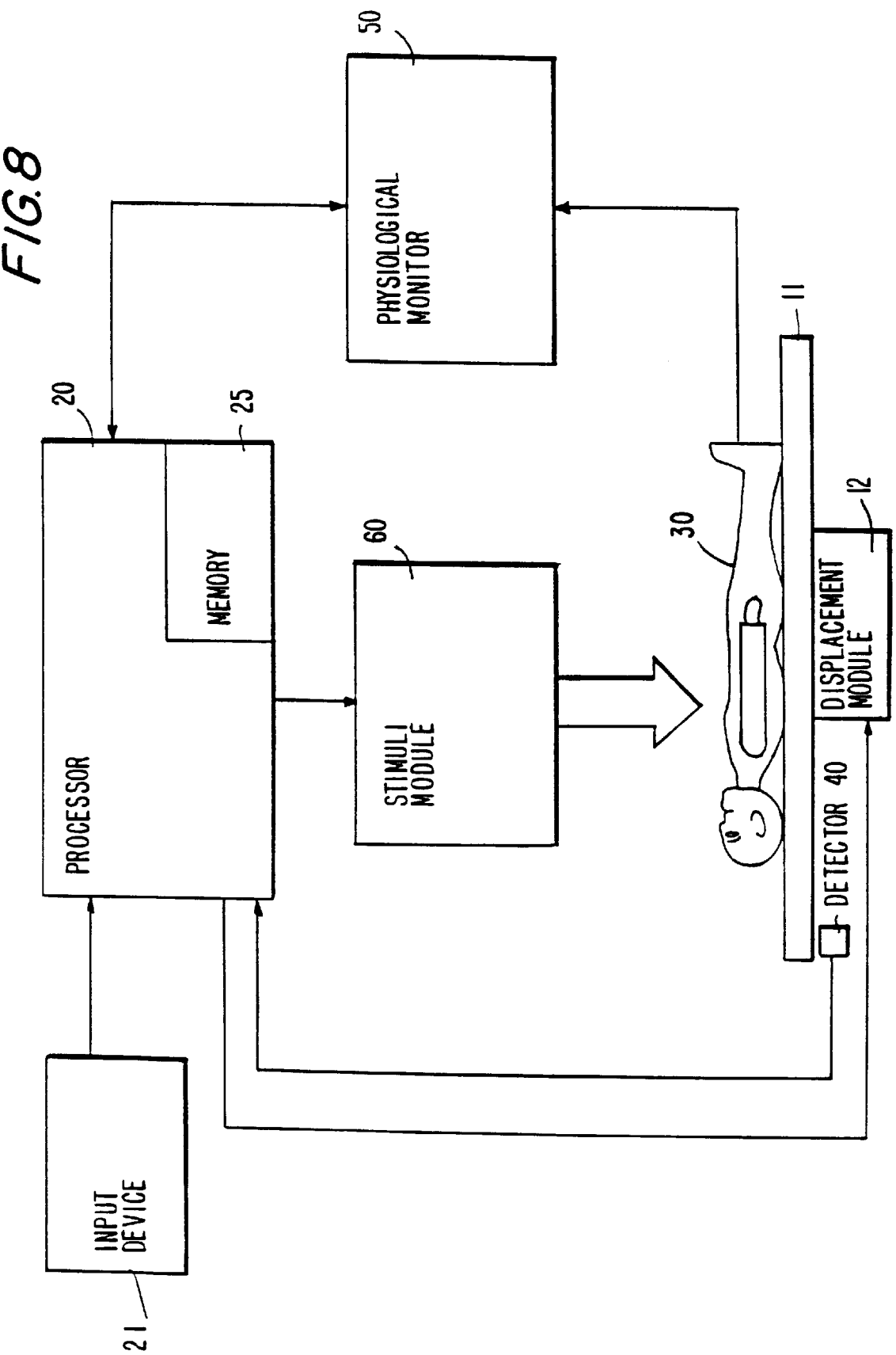

FIG. 10 Mechanical Ventilation Immediately After Intratracheal Meconium

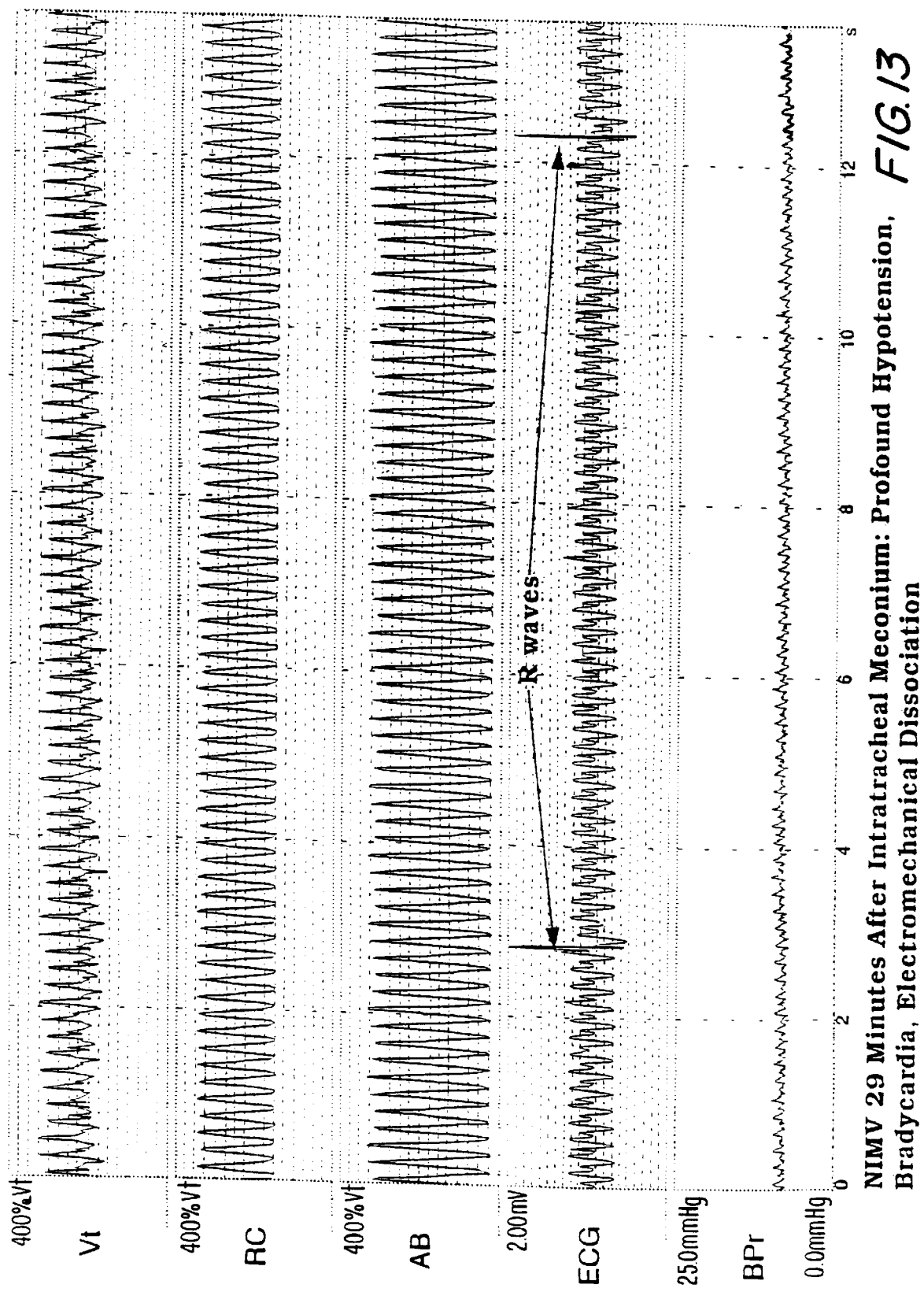
FIG. 13  NIMV 29 Minutes After Intratracheal Meconium: Profound Hypotension, Bradycardia, Electromechanical Dissociation

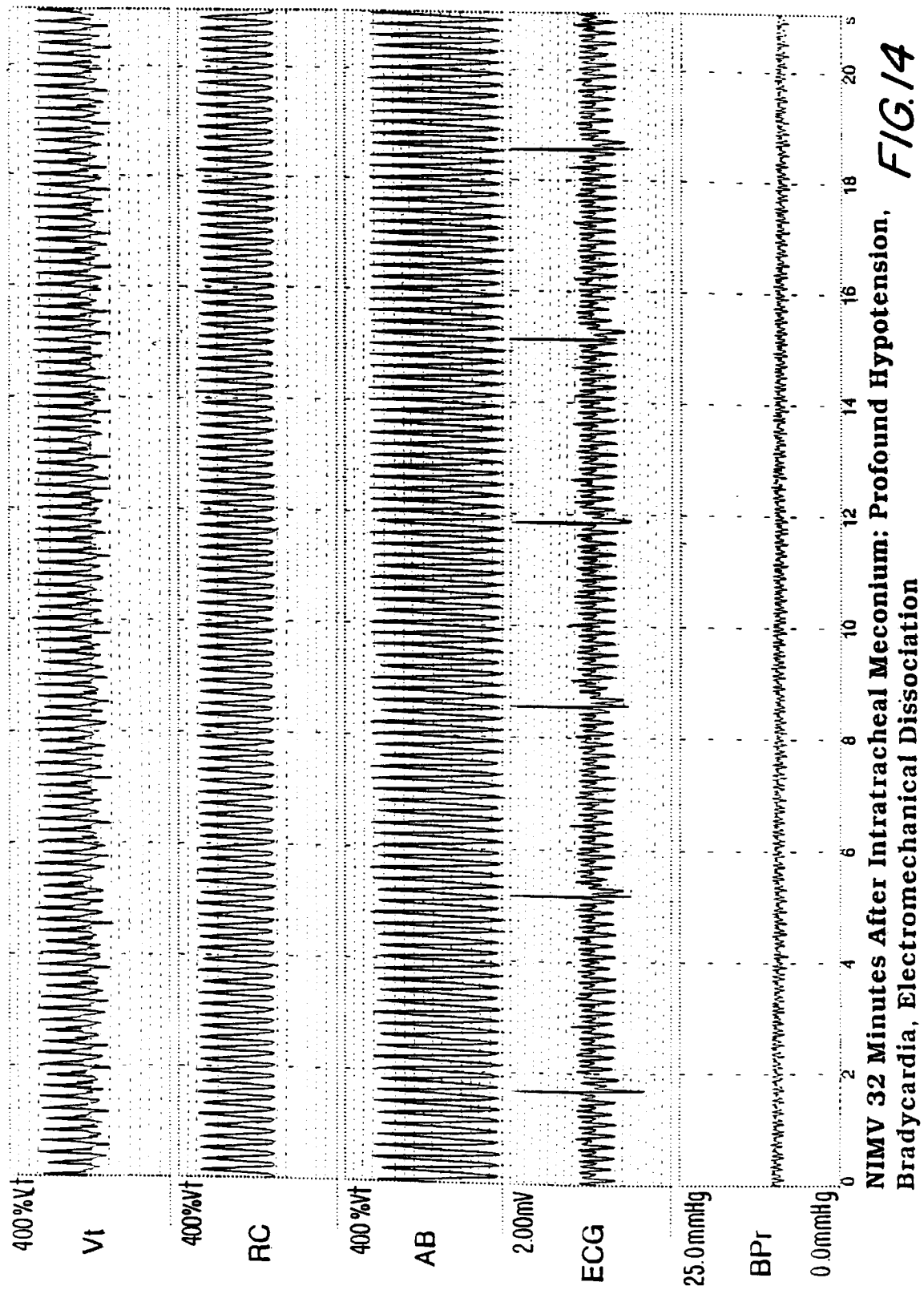
FIG. 14 NIMV 32 Minutes After Intratracheal Meconium: Profound Hypotension, Bradycardia, Electromechanical Dissociation

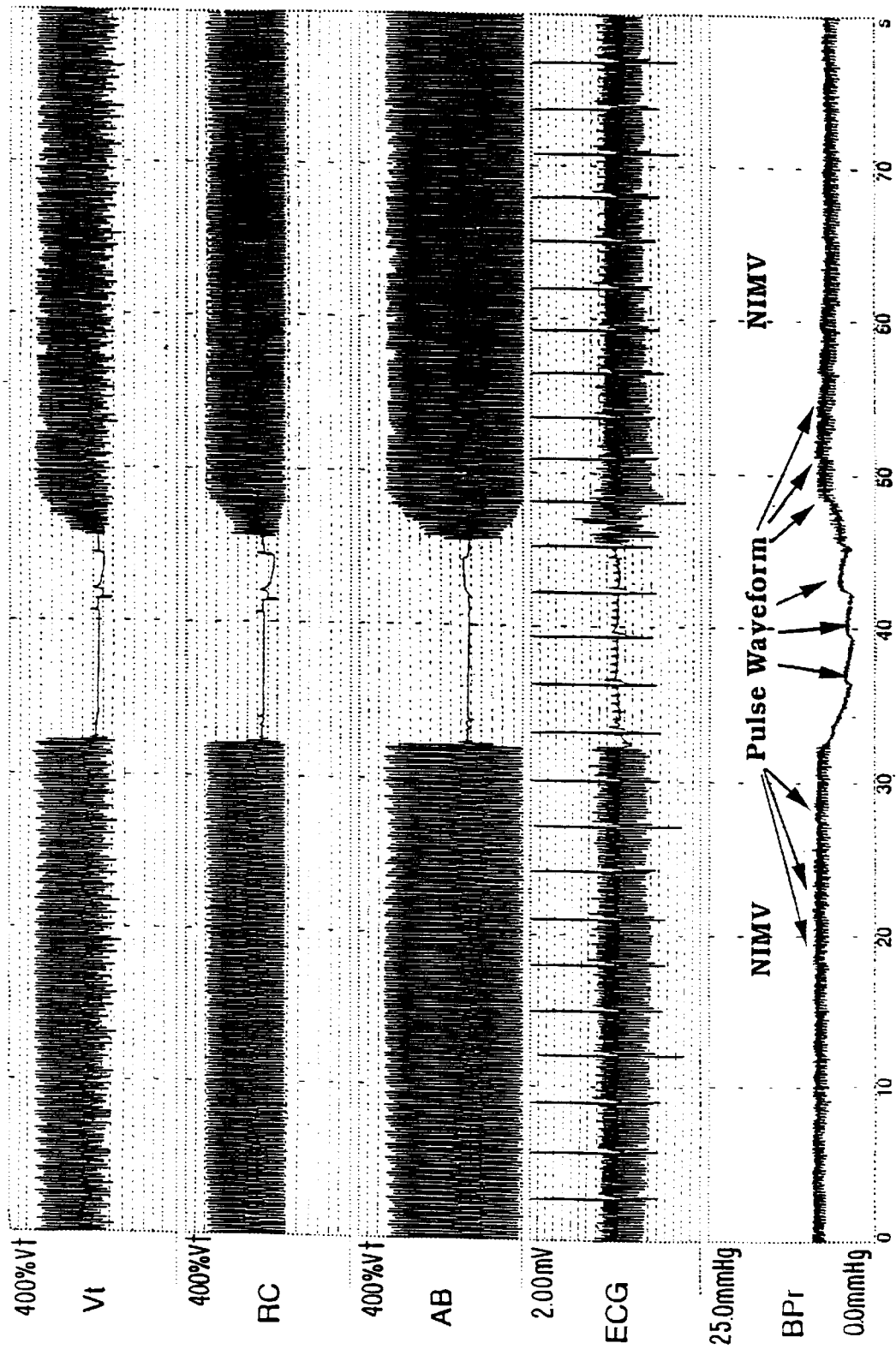

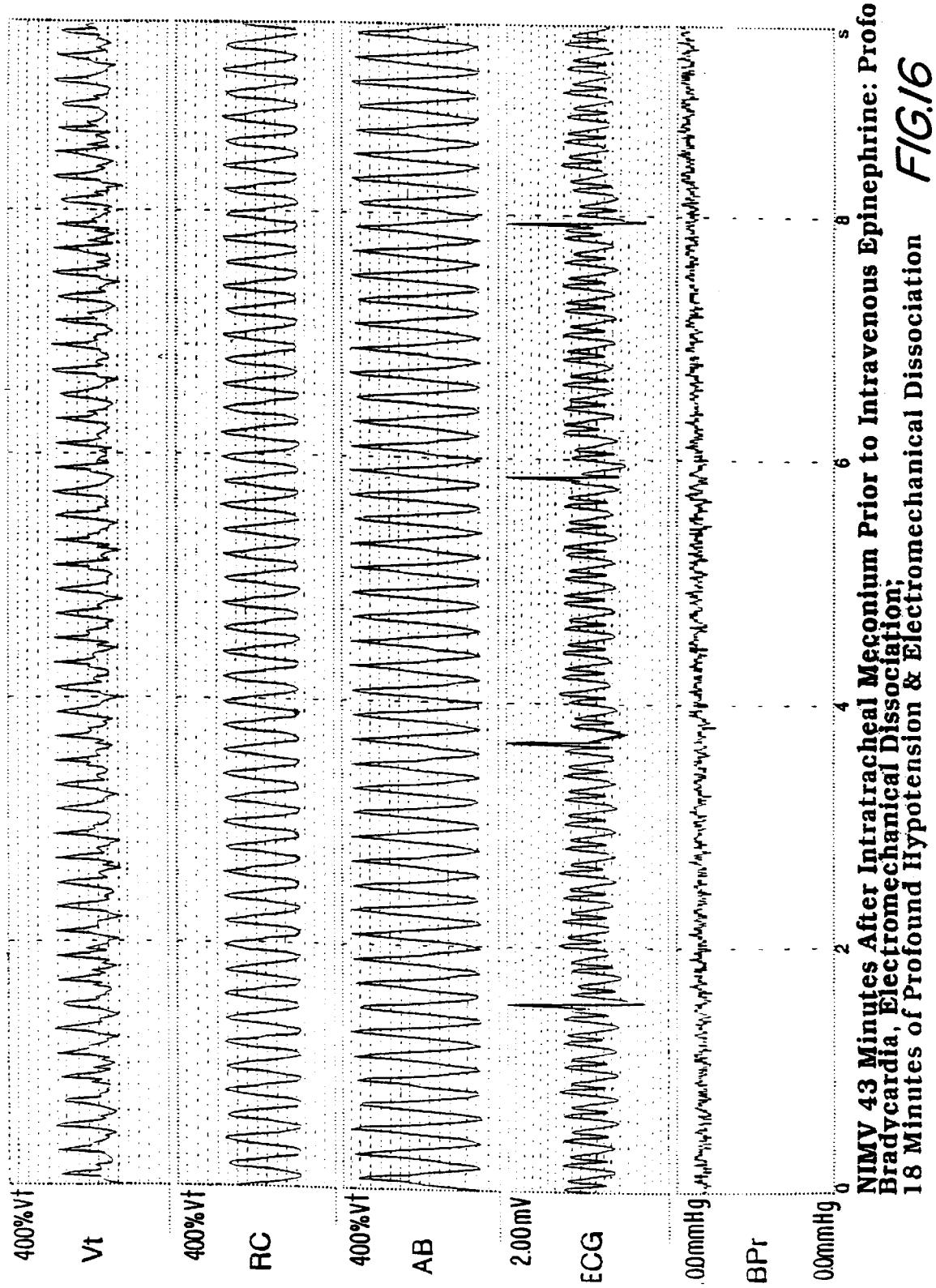
FIG. 16  NIMV 43 Minutes After Intratracheal Meconium Prior to Intravenous Epinephrine: Profo Bradycardia, Electromechanical Dissociation; 18 Minutes of Profound Hypotension & Electromechanical Dissociation

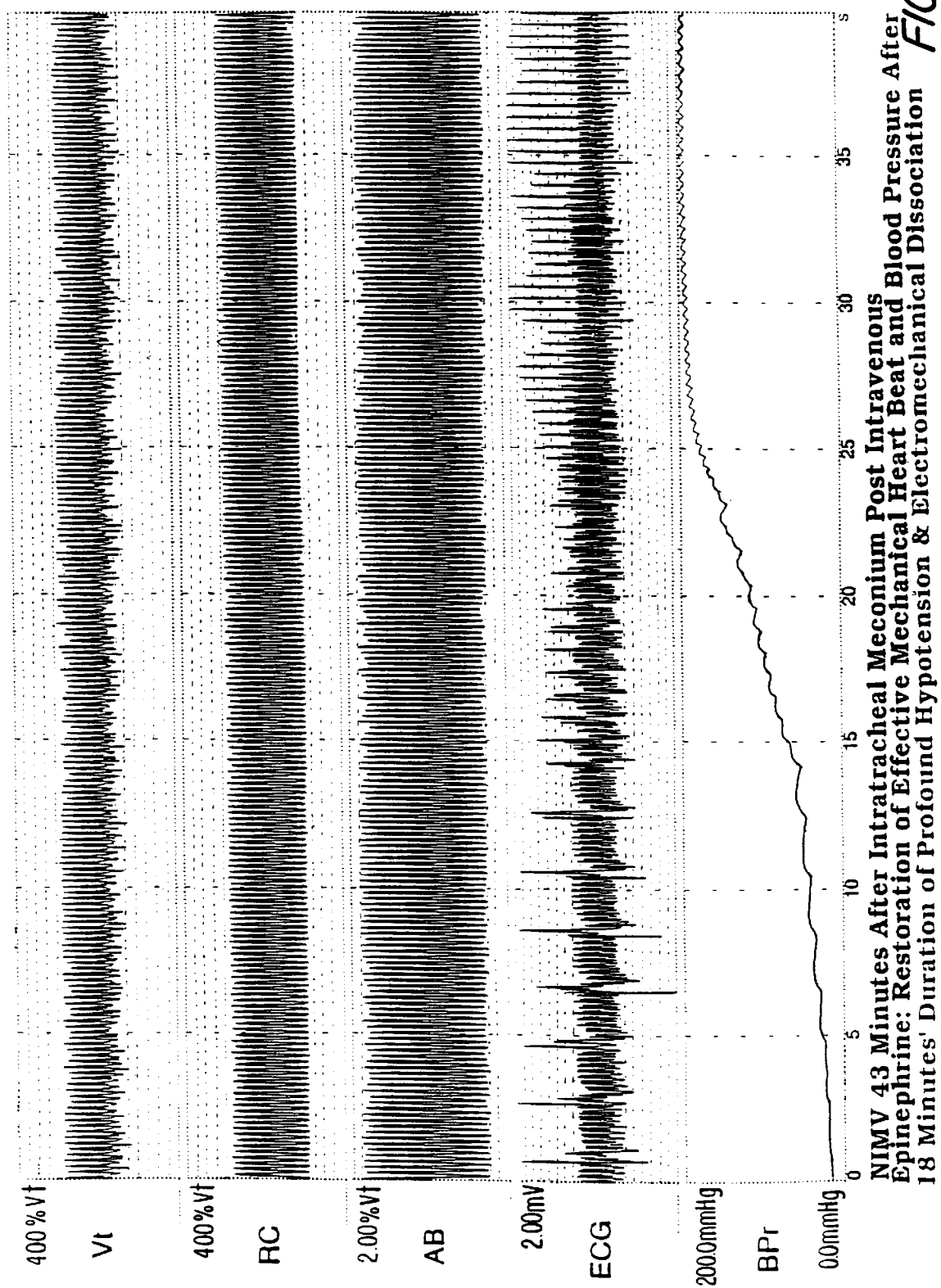
FIG. 17 NIMV 43 Minutes After Intratracheal Meconium Post Intravenous Epinephrine: Restoration of Effective Mechanical Heart Beat and Blood Pressure After 18 Minutes' Duration of Profound Hypotension & Electromechanical Dissociation

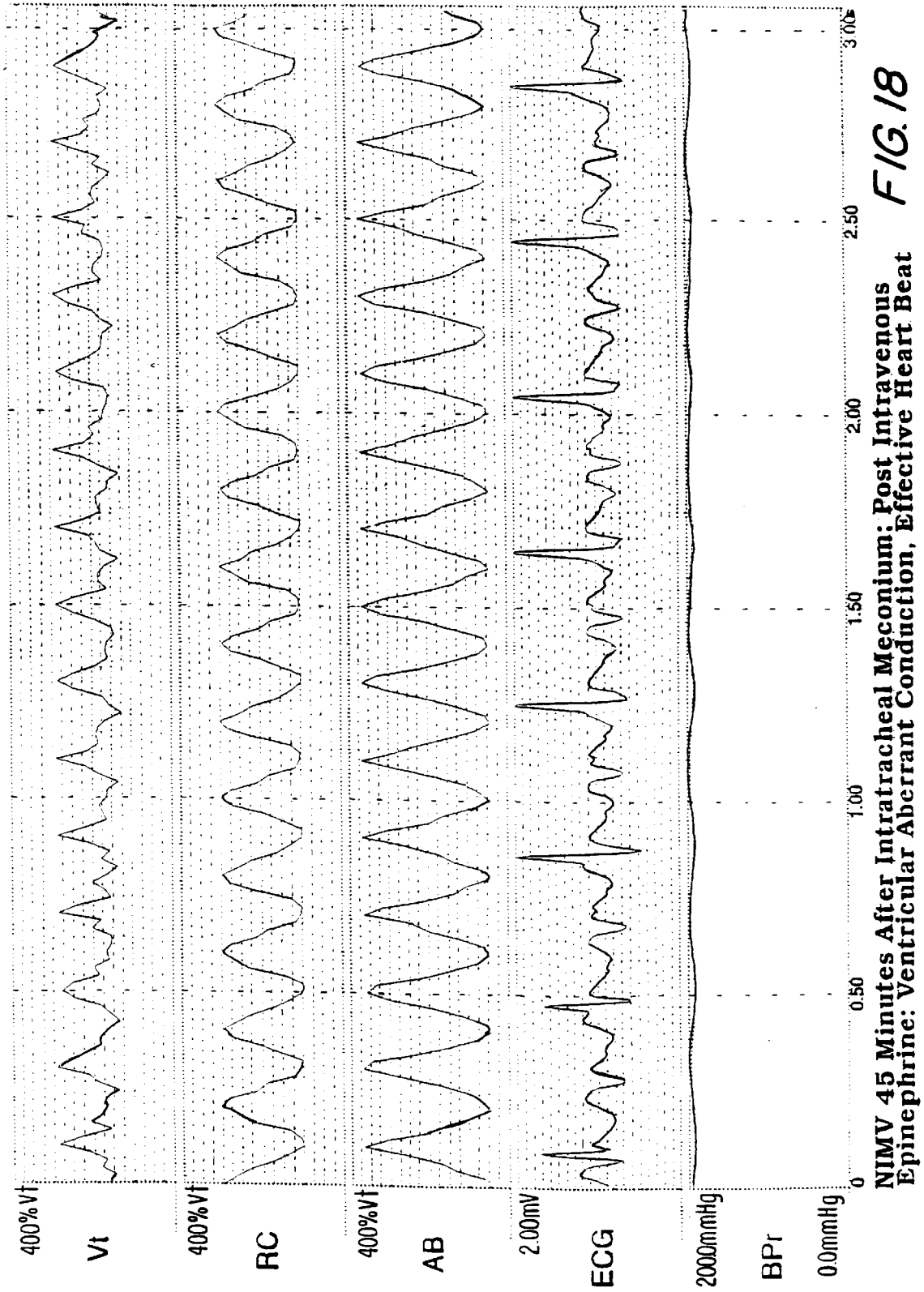
FIG. 18 NIMV 45 Minutes After Intratracheal Meconium; Post Intravenous Epinephrine: Ventricular Aberrant Conduction, Effective Heart Beat

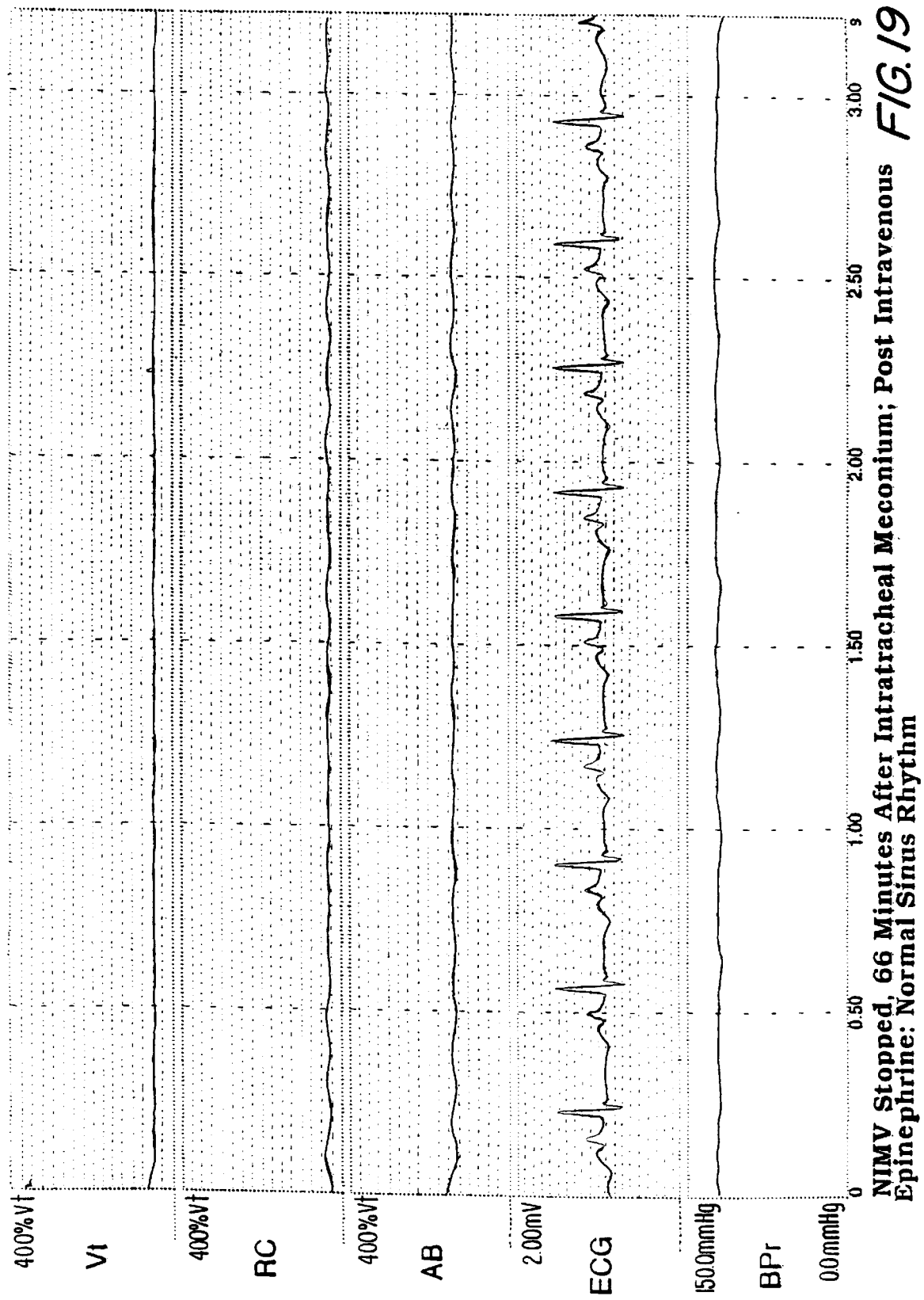

RECIPROCATING MOVEMENT PLATFORM FOR SHIFTING SUBJECT TO AND FRO IN HEADWARDS-FOOTWARDS DIRECTION

RELATED APPLICATIONS

This application is a Continuation-In-Part of U.S. Non-provisional Utility Application Ser. No. 09/041,578, filed Mar. 13, 1998 now abandoned, which claims priority from Provisional Application Nos. 60/040,457 filed Mar. 14, 1997 and 60/064,541 filed Nov. 15, 1997. The disclosures of the utility application and both of these applications are expressly incorporated herein by reference.

BACKGROUND OF THE INVENTION

1. Field of the Invention

The present invention relates to a platform assembly with a movable platform operable in an oscillatory motion so that a subject on the platform moves in a headwards and footwards direction with the platform. Currently contemplated applications of the invention will utilize variations in the speed, frequency and symmetry of oscillatory movement of the platform and include at least the following: sleep induction, apnea prevention, awakening functions, relief from restless legs syndrome and painful legs and moving toes syndrome, non-invasive motion ventilation, non-invasive vibratory ventilation, non-invasive cardiopulmonary resuscitation, non-invasive counter pulsation, augmentation of stroke volume, non-invasive cardiopulmonary bypass support, mediator release, and stimulation of bowel motility.

2. Description of the Related Art

It has long been recognized that many physiological characteristics such as breathing rates and heartbeats of humans and other animals are cyclic and that bodies respond to certain types of oscillatory stimulations with beneficial results. For instance, parents have long recognized that rocking a baby back and forth in a headwards-footwards direction soothes their child and hastens the onset of the infant's sleep. Many devices have been designed and marketed to accomplish this end. In addition to parental observation, scientific evidence indicates that babies have better developed proprioceptive-vestibular receptive systems than adults. This scientific evidence has been the basis for the development of devices which seek to soothe the baby in a simulated maternal development environment through such features as movements in a specially designed bed to simulate the mother's walking while the baby was a fetus, in conjunction with simulated sounding of maternal breath sounds, heart sounds and gastrointestinal sounds within such a system.

Furthermore, it appears that gentle, small oscillations on a waterbed may diminish the frequency of apneas in preterm infants. Prior art devices for preventing apnea include air mattresses with a bubble chamber, devices which induce auditory stimulation, devices which induce a vibration in a peripheral sensory area of the infant, a bed with a suspension and drive system to simulate motion experienced by a fetus while the mother is walking, and apparatus for producing mechanical vibrations which simulate the mother's heartbeat. These devices are passive in that they constantly produce their aural or mechanical stimulants. Others use non-invasive respiratory monitoring systems to trigger external stimulants to end an adverse cardiorespiratory event, such as an apneic event. Such triggered systems employ harsher rocking motions and vibrations to terminate the adverse cardiorespiratory events. For example, it is recommended that the baby be stimulated by touching and gently shaking to cause awakening and thereby terminate an apneic event.

As mentioned above, the breathing rate of a respiratory system is a cyclical physiological function of the body. Many forms of vibration and oscillatory stimuli which utilize the cyclical characteristics of the respiratory system are used for medical and/or experimental purposes. For instance, it is known that external chest vibrations in combination with tracheal gas insufflation, which is a form of high frequency vibration ventilation (HFVV), is an effective means of artificial ventilation in experimental animals. For example, when anesthetized paralyzed dogs are placed in the lateral decubitus position with their chest on a vibrating plate at a frequency of 15–30 Hz and an amplitude of 2–4 mm upward and downward, and a low flow of air is insufflated into the trachea at the level of the carina, adequate gas exchange is maintained. It has also been found that vibration of the chest wall reduces breathlessness. Vibration of the chest wall inspiratory muscles during inspiration (in-phase) reduces breathlessness associated with hypercapnia and resistive loading in normal subjects and patients with chronic obstructive lung disease. Vibration is typically applied using two standard physiotherapy vibrators—at a vibration amplitude of 2 mm at 120 Hz—manually triggered from the inspiratory flow signal displayed on a storage oscilloscope. However, no devices or methods are known where vibration or any other oscillatory motion alone will support ventilation.

Conventional positive pressure mechanical ventilators or positive pressure high frequency oscillatory ventilators support ventilation by repeatedly introducing volumes of air into the lungs and then releasing. A problem with these conventional methods of supporting ventilation is that a rather large pressure is required to inflate the lungs. The high positive pressure inflations of the lungs created by mechanical ventilators may damage the lungs in a phenomenon designated "barotrauma". Recent studies have made it apparent that lung injuries may also result from high tidal volumes or "volutrauma", the main determinant of which is the end-inspiratory volume. A ventilator that adequately exchanges gasses in the lungs and that requires less pressure in the lungs would reduce the effects and/or the occurrences of "barotrauma" and "volutrauma". High frequency oscillation ventilation is used with reduced acute and chronic lung injury. However, conventional high-frequency oscillation ventilation requires the insertion of an intubated airway which may not be appropriate under some of the circumstances in which mechanical ventilatory support is required.

The heart beat is another cyclical physiological function of the body. Many medical procedures, such as cardiovascular resuscitation, take advantage of the cyclical nature of the heart rhythm. Although many manual and automatic methods have been utilized for cardiopulmonary resuscitation, the perfect method has yet to be described. Active mechanical compression and decompression is the most recent method to be advocated; its advantage over standard compression is that the addition of active decompression facilitates venous return as intrathoracic pressure becomes negative relative to atmospheric pressure. And recently, a CPR method using a phased chest and abdominal compression-depression with a Lifestick® resuscitator for CPR was reported; this method suggests that active compression and decompression of both the thorax and abdomen with a phase shift of 180° is optimal, and subsequent trials have suggested that further improvement could be attained with a phase shift of 240°.

Another medical procedure which utilizes the cyclical nature of the heart beat and used for improving blood flow is called external enhanced counterpulsation, the goals of which are to decrease the pressure generated by the myocardium during systole and to augment the function of the compromised myocardium by increasing coronary blood flow. External enhanced counterpulsation is performed by compressing the vascular beds within the muscles of the legs and thighs, including the buttocks, in a sequential manner progressing from the calves to the lower and then the upper thighs. This procedure is accomplished by placing and selectively inflating air inflatable bladders around the limbs. Timing of compression is controlled by an electrocardiogram, with the activation of a bladder compression in the vicinity of the electrocardiographic T wave (diastole). This causes increased blood flow and pressure to reach the coronary vessels in diastole at the lowest intramyocardial tension. Compression also increases venous return and cardiac output. The external pressure is then released during the next subsequent R wave (systole), causing systolic unloading and decreasing cardiac work. This treatment improves survival in patients with cardiogenic shock after myocardial infarction, to significantly reduce mortality during acute myocardial infarction, and to improve hemodynamics in chronic angina pectoris. However, the process is complex.

Yet another procedure that takes advantage of the cyclical nature of the heart rhythm is high frequency jet ventilation to augment cardiac stroke volume. Because both systemic venous return and factors determining left ventricular performance may vary over the cardiac cycle, phasic increases in intrathoracic pressure, as produced by high frequency jet ventilation, may differentially affect ventricular preload or afterload if delivered at specific points in the cardiac cycle. When contractility is normal, selective increases of intrathoracic pressure at end-diastole minimally impairs ventricular loading and causes mild hemodynamic deterioration. When cardiac contractility is inpaired and filling pressures elevated, selectively increasing intrathoracic pressure during systole is associated with increased stroke volume despite decreases in left ventricular filling pressure. In acute mitral regurgitation, increasing intrathoracic pressure by increasing the pressure gradient for left ventricular ejection augments cardiac output. This has been demonstrated by utilization of high frequency jet ventilation triggered off either cardiac systolic or diastole in an animal model. As compared with conventional positive pressure mechanical ventilation, systolic synchronous jet ventilation induced a greater increase in stroke volume than diastolic synchronous jet ventilation. However, this procedure is also very complex and is highly invasive to the subject on which it is being performed.

Recently, a large body of evidence has accumulated indicating that increases in the amplitude and frequency of blood flow and intravascular shear stress enhance vascular function and structure. One method for increasing the cycle of blood flow and intravascular sheer stress is exercise. Increases in shear stress on the vascular endothelium caused by increases in blood flow and pulsatility lead to an increase in the release of beneficial mediators such as nitric oxide, prostacyclin, renin, and tissue plasminogen activator. Decreased shear stress causes less of these mediators which promotes development of arteriosclerotic lesions. It is believed that exercise-induced increases in blood flow and shear stress, by increasing the release of nitric oxide and prostacyclin, augment endothelium-dependent vasodilation and inhibit multiple processes involved in atherogenesis and restenosis. Congestive heart failure, which is marked by decreased cardiac output, results in reduced shear stress on the endothelial cells and less beneficial mediator release. As mentioned above, the best way to maintain proper levels is to exercise; however, it is difficult for some people to exercise because of either physical constraints or respiratory problems.

Another problem precipitated by rest is restless legs syndrome and painful legs and moving toes syndrome. Restless legs syndrome is a common problem that is precipitated by rest and relieved by activity. It is treated with a variety of medications, all of which have major side effects.

Finally, according to the National Digestive Diseases Information Clearing House on Constipation, lack of exercise can lead to constipation. Constipation often occurs after an accident or during an illness when one is bedridden and cannot exercise.

SUMMARY OF THE INVENTION

It is an object of the present invention to provide a reciprocating movement platform that is operable for rocking a subject in a headwards and footwards direction to induce the onset of sleep, to prevent or minimize apneas, to rapidly shake the subject in the headwards and footwards directions for waking the subject if the subject is experiencing an adverse cardiorespiratory event, to relieve the effects of restless legs syndrome and painful legs and moving toes syndrome, to oscillate the subject in the headwards and footwards directions for non-invasive motion ventilation, non-invasive vibratory ventilation, non-invasive cardiopulmonary resuscitation, non-invasive counter pulsation, augmentation of stroke volume and non-invasive cardiopulmonary bypass support, to alleviate breathlessness in patients with chronic obstructive lung disease and chronic heart failure, to produce release of mediators from the endothelial linings of blood vessels, and to stimulate bowel motility and a method for achieving these results.

The platform comprises a board formed of a stiff material on which a mattress or other type of cushioning object may be placed. The platform is movably connected to a frame using displacement modules that operatively move the platform in a headwards and footwards direction. The displacement modules may comprise electric or pneumatic solenoids. The modules may also comprise an AC or DC motor with a linear shaft, a hydraulic actuator or a flywheel with an eccentric mass. The movement characteristics of the platform are controlled by the displacement modules with control signals originating from a processor to control the amplitude, frequency and acceleration of movement. The processor further comprises a memory in which may be stored motion templates which include information relating to specific types of motions. For instance, a specific oscillatory motion for inducing sleep based on the rocking motion of carriages and/or patting a baby to sleep can be stored in the memory. The platform may also be gently rocked to prevent apneic events. These motions of the platform may be manually adjusted to suit individual subjects. The adjusted motions may be recorded using a detector such as an accelerometer, or any other type of detector for indicating the motion characteristics of the platform such as a speedometer or a position detector, by downloading the information from the detector to the processor memory. The recorded characteristics of the motion may thereafter be accessed for recreating that particular motion at a later time. Signals from the detector may be used as a measure of quality control of the effectiveness of the platform. The detector may also be used as a safety device whereby the processor discontinues movement of the displacement modules when platform movement causes the output of the detector to exceed a predetermined limiting value. Instead of using preset templates, the motion of the platform may also be manually adjustable by dynamically varying the characteristics of the motion, such as its frequency, amplitude, and acceleration, during the reciprocal movement using an input device for determining the type of the motion.

The platform assembly optionally includes a monitoring device for triggering a specific motion of the platform upon the occurrence of an event. In a simple embodiment, the event could be the crying of a baby; in that case, the monitor may be a microphone and the processor may initiate a gentle rocking motion of the platform if a preset audio level is exceeded. The event could also be an adverse cardiorespiratory event, such as central, mixed, and obstructive apneas, prolonged apnea, pulse waveform validated arterial oxygen saturation, heart rate changes from an electrocardiogram, severe hypoxemia, and/or severe bradycardia. The processor responds to this event by rapidly shaking the platform to wake the subject and end the adverse event. If the adverse event is not terminated by the shaking, the additional stimulatory modules or functionality may be activated serially or in parallel to the shaking. The additional stimulatory modules may include a strong light source directed at the face of the subject, a voice sound calling the subject to wake up, and/or a pulsating air column directed onto the skin. Other types of stimuli directly contacting the subject may also be used. However, the preferred method for terminating this type of adverse event is to employ stimuli that do not directly contact the subject so as to avoid potential trauma caused by devices acting in direct contact with the body.

The device for monitoring these adverse events preferably incorporates Respitrace® technology (respiratory inductive plethysmography), electrocardiography, and pulse wave validated pulse oximetry. Other non-invasive, torso placed breathing monitors such as magneto meters, strain gauges, bellows pneumographs, linear displacement transformers, inductive circumferential transformers, and two channel impedance pneumographs.

The reciprocating platform of the invention is also operable for oscillating in the range of +0.25−+1.5 Hz at an amplitude of approximately 1.5–2.5 cm and with peak accelerations of 0.25 g to 1.0 g, to provide an assisted ventilation and/or as a source of ventilation for the subject. The platform is additionally operable for supporting ventilation or assisting ventilation at the frequency of normal breathing rates, and can also be vibrated at high frequencies (15–30 Hz) and low amplitudes (0.2–0.5 cm) to alleviate dyspnea in lung disease and as an aid in tracheal gas insufflation. Prior art devices for inducing vibrations include only small vibrating devices placed on or below the torso of the subject; the platform of the present invention, however, induces vibration throughout the entire chest area and thereby greatly enhances the effects of the vibration.

At the high frequency oscillations 0.25–15 Hz, the platform also 1) increases synthesis in the alveoli and release of surfactant into the airways from the alveoli, 2) evenly distributes pharmacological agents within the lungs, and 3) a clears retained bronchopulmonary secretions by oscillatory two-phase gas-liquid interaction.

The oscillations of the reciprocating platform at 0.25–15 Hz also serve as cardiopulmonary or cardiac support for 1) cardiopulmonary resuscitation, 2) counterpulsation, 3) augmentation of cardiac stroke volume, and 4) non-invasive cardiopulmonary bypass.

Finally, the oscillatory motion of the platform may substitute for the beneficial effects of exercise by promoting endothelial shear stress which promotes endogenous nitric oxide release for treatment of entities in which that molecule is indicated. These entities include among others, septic shock, chronic heart failure, cerebrovascular accidents, and pulmonary hypertension. The motion platform may also aid in the prevention and treatment of restless legs syndrome, and aid in the prevention and treatment of constipation in bedridden patients.

The various features of novelty which characterize the invention are pointed out with particularity in the claims annexed to and forming a part of the disclosure. For a better understanding of the invention, its operating advantages, and specific objects attained by its use, reference should be had to the drawings and descriptive matter in which there are illustrated and described preferred embodiments of the invention.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

BRIEF DESCRIPTION OF THE DRAWINGS

In the drawings, wherein like reference characters denote similar elements throughout the several views:

FIG. 8 is a block diagram of the control circuit for the platform assembly of the present invention;

FIGS. 10–19are a series of graphs showing the physiologic waveforms for a third piglet during NIMCPR.

DETAILED DESCRIPTION OF THE PRESENTLY PREFERRED EMBODIMENTS

Figure 1:
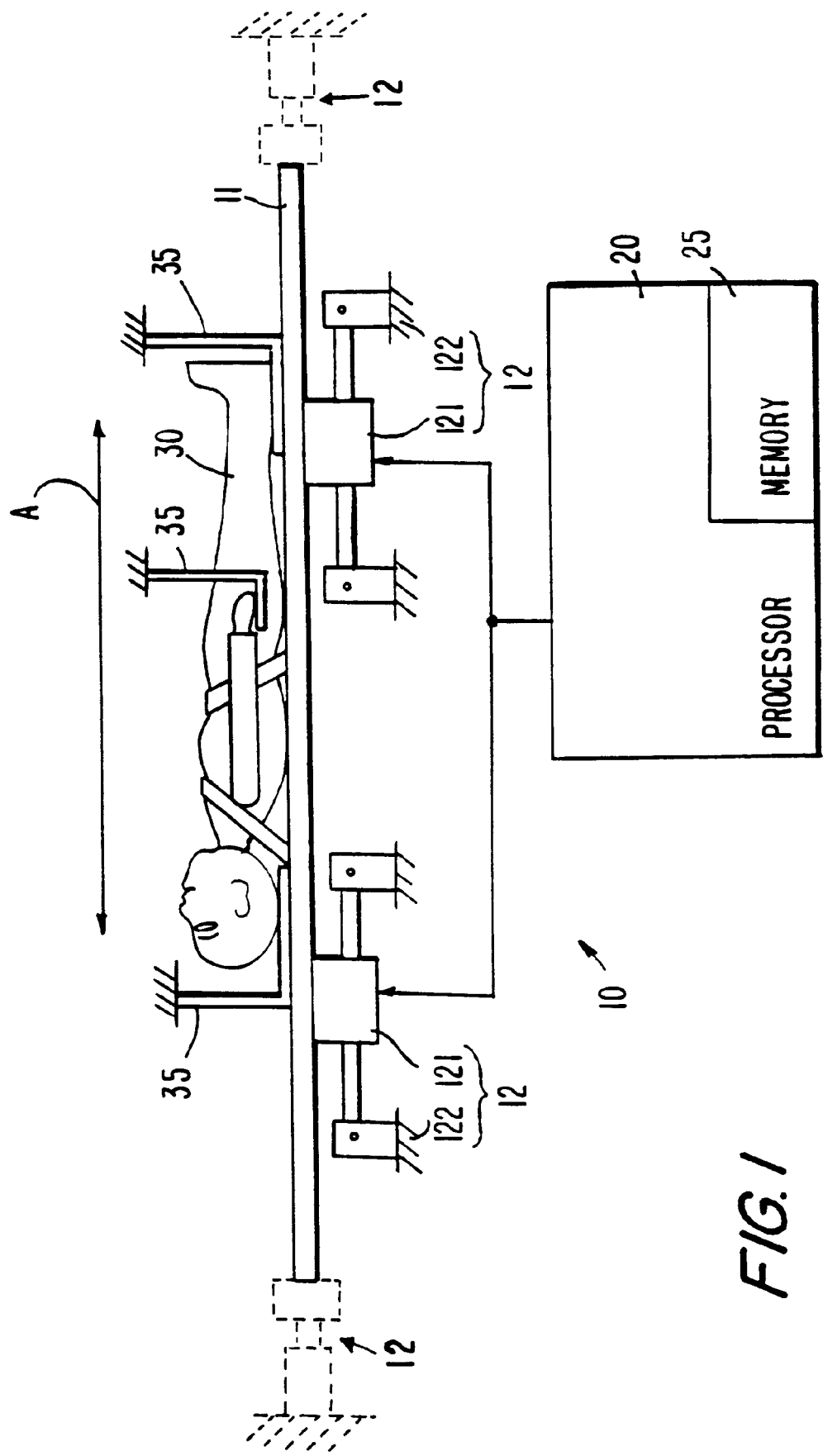
FIG. 1 is a schematic diagram of an embodiment of the platform assembly of the present invention.

Referring initially to FIG. 1, a platform assembly 10 of the present invention for oscillating a subject in a headwards and footwards direction A—i.e. parallel to or along the longation or length of the subject's body—comprises a platform 11 mounted on displacement modules 12. A fixed portion 122 of each displacement module 12 is fixedly connected to a support frame (not shown in FIG. 1). A movable portion 121 of each displacement module 12 is connected to platform 11. The platform 11 may be constructed of any stiff material such, for example, as plywood, metal, or compressed particle board. The displacement modules 12 may take the form of any device operable to controllably effect the desired oscillatory motion of the platform 11 and may, by way of example, be implemented by electric or pneumatic solenoids, AC or DC motors with a linear shaft, or hydraulic actuators.

In the FIG. 1 side view of the platform 11, only two displacement modules 12 are shown. In the preferred embodiment, two additional displacement modules 12 are positioned symmetrically on the side of the platform 11 that is visible in FIG. 1 (i.e. at the four corners of the platform). However, instead of four displacement modules 12, the platform assembly 10 may alternatively comprise a single displacement module 12, as long as the platform 11 is sufficiently supported throughout its reciprocal motion. For instance, the platform may be connected to a single displacement module 12 for moving the platform in an oscillatory motion and the platform may additionally be supported by passive sliding supports to stabilize the platform throughout its oscillatory motion.

Instead of placing the displacement modules at the bottom of the platform, the modules 12 may be located at the ends of the platform (as shown in dotted lines in FIG. 1) so that they operatively push and pull the platform to effect the intended oscillatory motion. In this alternate arrangement, the displacement modules 12 may be supportably connected to platform 11, or platform 11 may be separately movably supported on sliding elements. This modified arrangement is particularly well suited for platforms in which a frame surrounds the platform, as in conventional beds and particularly in cribs. Also in this embodiment, the displacement modules are connected between a platform which supportedly receives a mattress and a bed frame of the conventional bed or crib.

The displacement modules 12 are depicted as generating linear oscillatory motion of the platform 11 in the headward and footward directions depicted by double arrow A. However, the displacement modules 12 may also be connected for providing other types of motion such as along an arc. Similarly, the motion may also follow a circular, elliptical, or any other shaped path.

A subject 30, such as an infant or an adult, may be placed directly on the platform 11 as shown in FIG. 1. Alternatively, a mattress or other type of cushioning material (not shown in the drawings) may be placed on the platform 11 between the upper surface of the platform 11 and the subject 30, so that the subject 30 lies in a more comfortable environment. Optionally, the platform assembly 10 may be integrated with a conventional crib or bed. The subject 30 may be held onto the platform 11 with a harness 18. In an alternate embodiment, the head, legs and arms of the subject 30 are removed from direct contact with the platform 11 and are supported by supports 35 that lift them away from platform 11. The supports 35 may comprise slings or pedestals that are adjacent to but separated from the platform 11 to support the subject's head, neck, arms, and legs. In this way, only the torso of the subject 30 is directly affected by the motion of the platform 11.

Figure 1A:
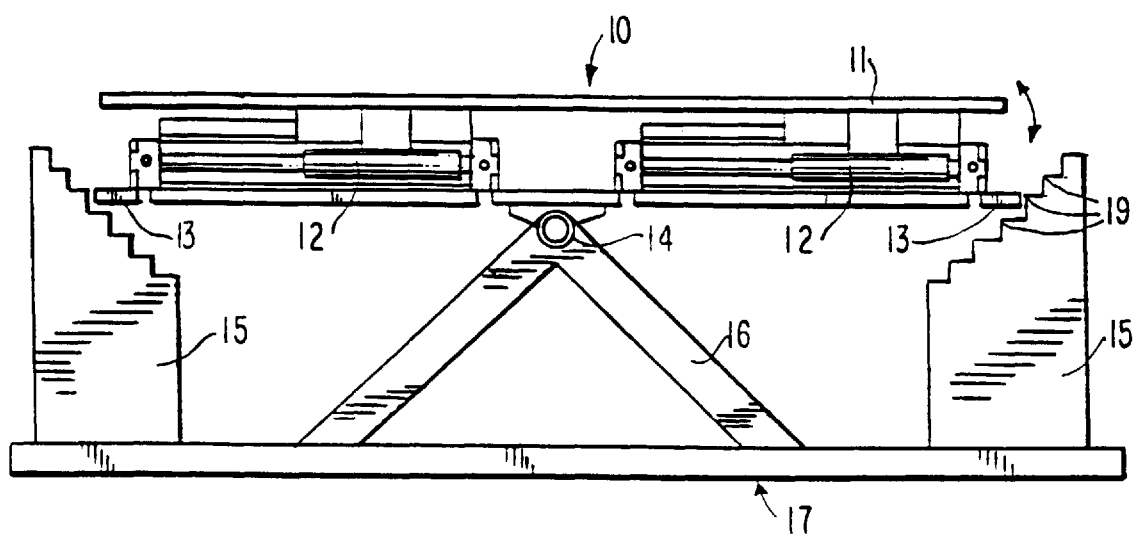
FIG. 1a shows a more detailed view of the platform, the displacement modules, and the frame of the assembly of FIG. 1.

Referring now to FIG. 1a, the platform assembly 10 may include side mounts 13 and a central mount 14 for fixedly connecting the displacement modules 12 to a support frame 17. The frame 17 is shown as having a pair of stepped supports 15 on which the side mounts 13 rest and a fulcrum support 16 to which the central mount 14 is pivotally connected. Each of the stepped supports 15 includes a plurality of steps 19 to which the side mounts 13 are supportably connectable. The position of stepped supports 15 is adjustable so that the platform 11 is selectively tiltable with respect to the frame 17 by ±/−18° and can be fixed in a tilted orientation. Thus, the subject 30 on platform 11 may have his or her head, or feet, elevated relative to the other. FIG. 1a shows the platform 11 in its central substantially horizontal position.

Figure 1B:
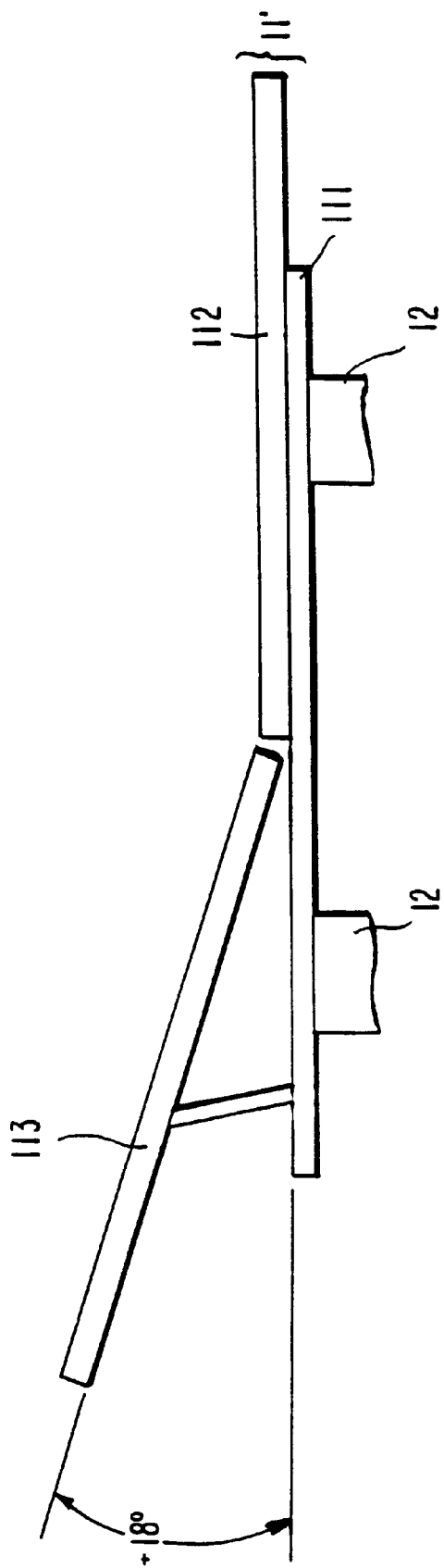
FIG. 1b depicts another embodiment of the platform of the assembly.

Instead of tilting the entire platform 11, portions of platform 11 may be inclined so that only the subject's upper body, or feet, are inclined. The embodiment shown in FIG. 1b includes a platform 11' having a support portion 111 and two separately inclinable platform sections 112, 113 each individually inclinable, for example, by +18°. FIG. 1b illustratively depicts platform section 113 in the fully inclined position. Although sections 112 and 113 are shown as inclinable upward, they may also be inclined downward from their horizontal position.

Figure 2A:
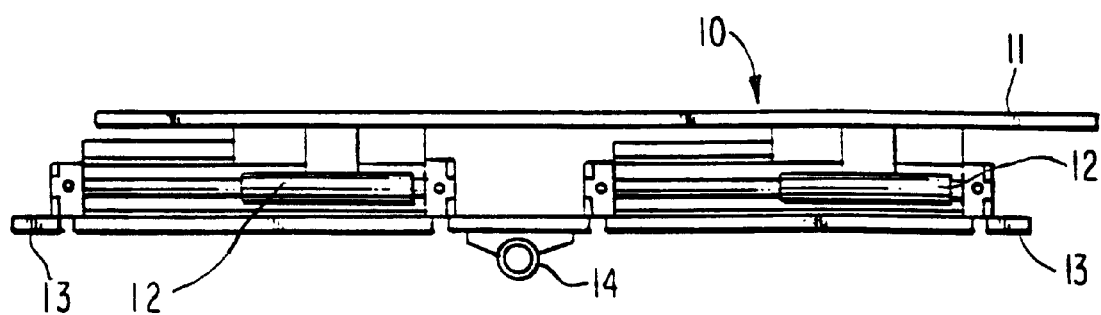
FIGS. 2a and 2b show the displacement modules and platform of the assembly of FIG. 1 at the extreme right and extreme left displaced positions.
Figure 2B:
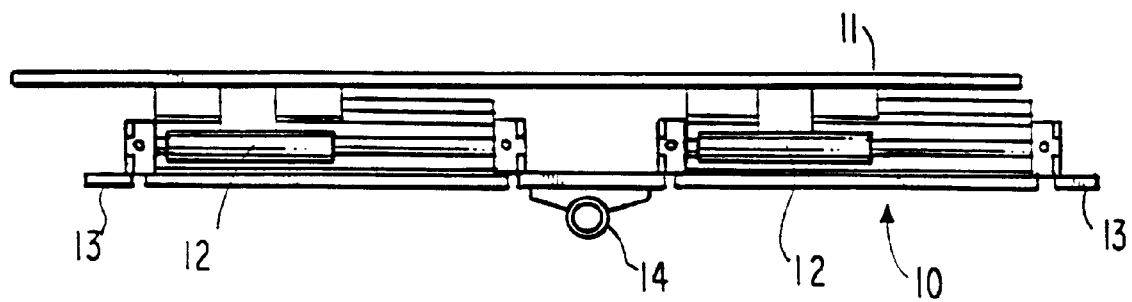

Referring now to FIGS. 2a and 2b, the displacement modules 12 may alternatively comprise double acting rodless air cylinders that can be mounted therebeneath, as for example Origa NR50-32-2020/50×6-B-M (Origa Corporation, Glendale Heights, Ill. 60138-4818) or similar cylinders. The amplitude, frequency, and waveform characteristics of the motion of the rodless air cylinders connected to the platform are controlled in the disclosed form of the invention by 24V solenoid operated piloted pneumatic valves such as Mac 52A-14-BOA-DM-DDFJ-IJB-416Y (Mac Valves, Inc., Wixom, Mich. 48393-2892) or similar valves. In this particular embodiment, the displacement modules 12 comprise both the rodless air cylinders and the pneumatic valves. The modules 12 are preferably DC motors to take advantage of their fast on/off response times; one such DC motor that may be used in the APS 113 Electro-Seis and its matching power amplifier APS 124 (APS Dynamics, Inc., Carlsbad, Calif. 92008). FIG. 2a shows the maximum displacement of platform 11 to the right with respect to the displacement modules 12, and FIG. 2b shows the maximum displacement of the platform 11 to the left.

Figure 3B:
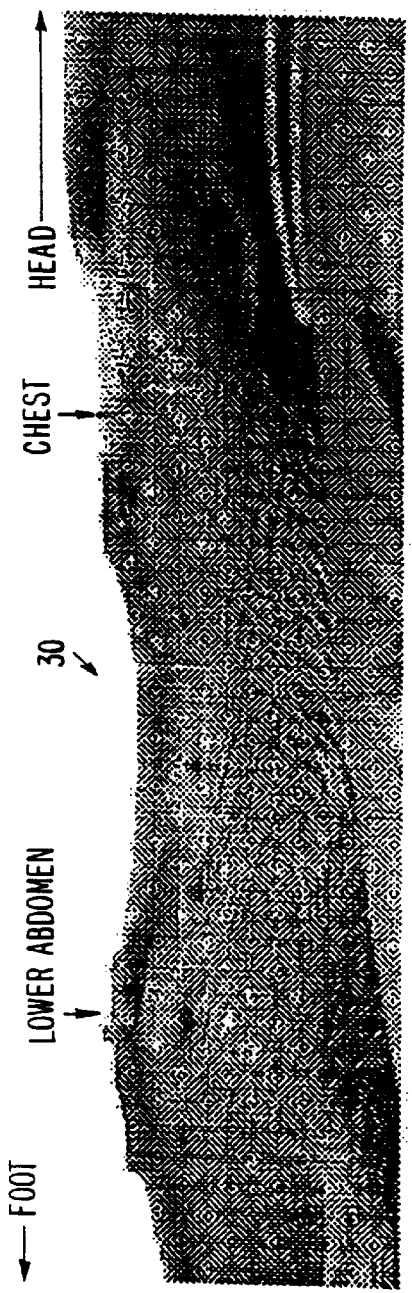
FIG. 3a and 3b show a subject on the platform at the operating positions of the platform shown in FIGS. 2a and 2b, respectively.
Figure 3A:
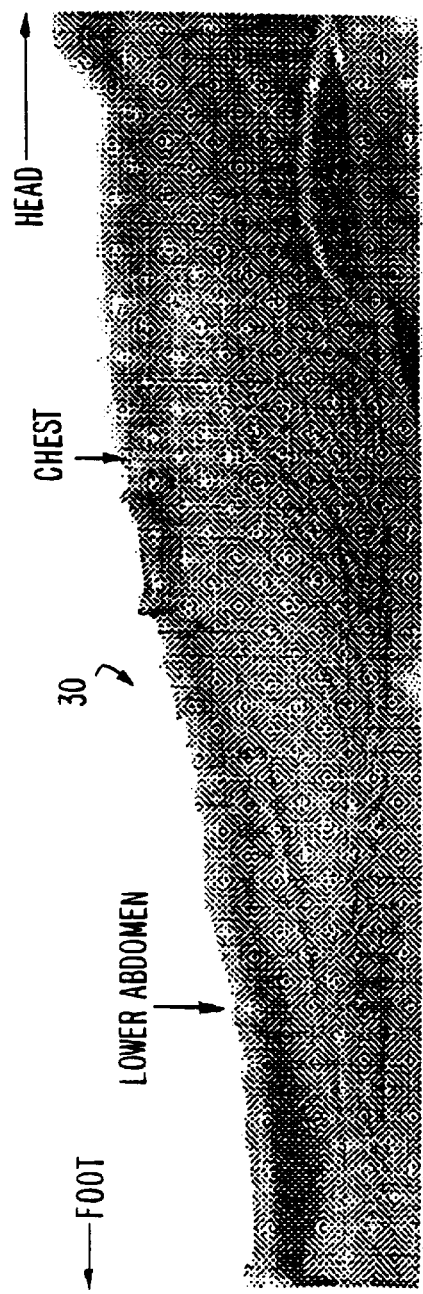

FIGS. 3a and 3b respectively depict a side view of a supported subject 30 at the maximum displacement positions of the platform 11. The motion of the platform creates a paradoxical movement of the subject's abdomen and chest; that is, one direction of the motion causes the abdomen to move sufficiently outward and the chest to move sufficiently inward, while the opposite direction of motion causes the opposite effect.

Figure 4:
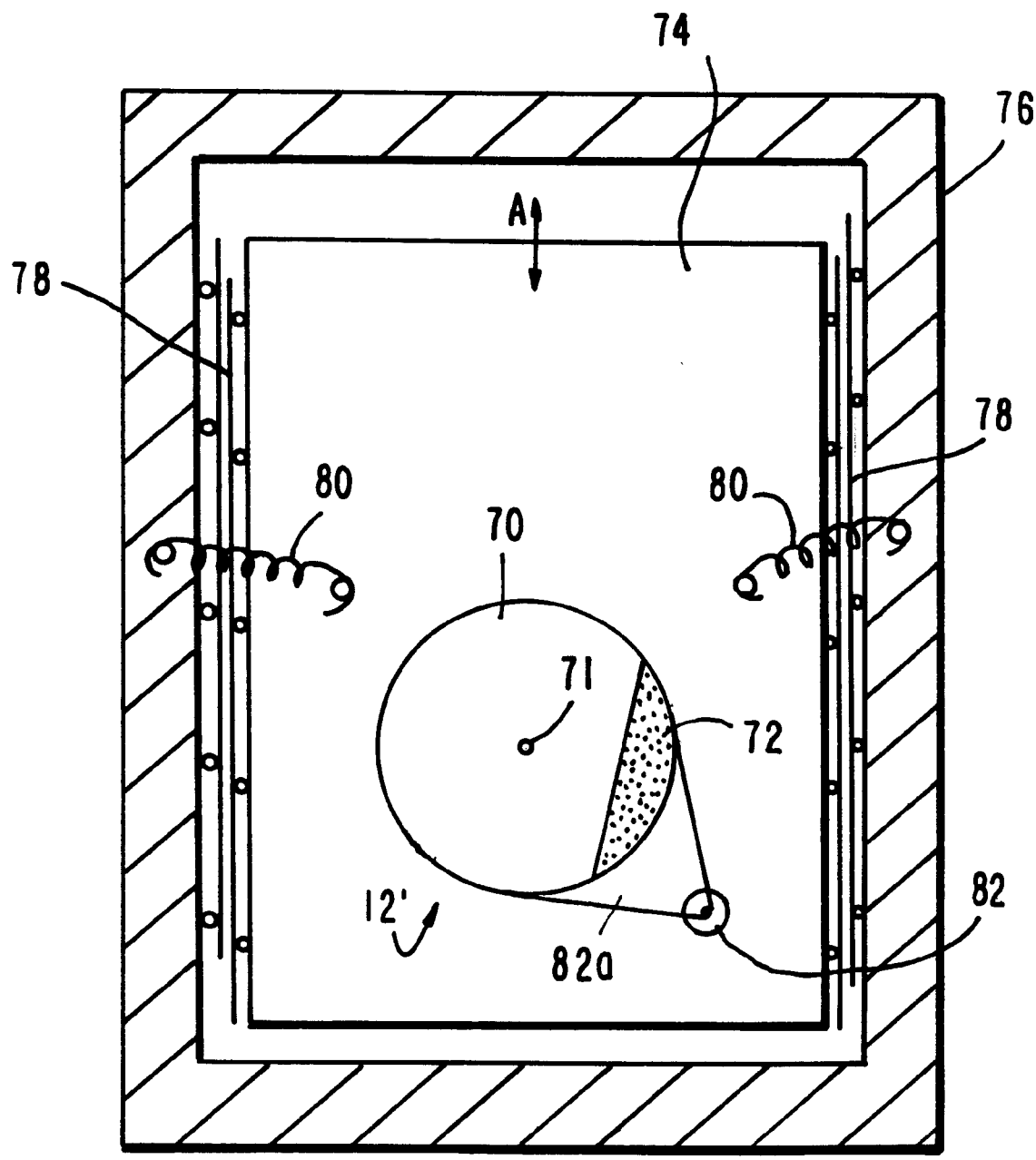
FIG. 4 shows another embodiment of a displacement module having a flywheel and platform.

FIG. 4 shows another embodiment of a platform assembly 10' according to the present invention in which a displacement module 12' includes a flywheel 70 having an eccentric mass 72. In this embodiment, platform 74 is mounted in a stationary frame 76 via linear slides 78 which allow the platform 74 to move relative to the stationary frame 76 in the direction of the linear slides 78, as indicated by arrow A. Springs 80 are connected between the stationary frame 76 and platform 74 to hold platform 74 at a default position relative to stationary frame 76. The rotatable flywheel 70 having the eccentric mass 72 is rotatably mounted to platform 74. A small motor 82 is connected to flywheel 70 for rotating the flywheel 70 and the eccentric mass 72 either directly or via a belt 82a, as shown in FIG. 4. The rotation of eccentric mass 72 causes platform 74 to slide back and forth along the linear slides 78 in the directions indicated by arrow A at oscillatory frequencies that range from about 0.25 Hz to 15 Hz, amplitudes that range from about 1.5 to 2.5 cm, and peak accelerations that range from about ±0.25 g to ±1.5 g. The springs 80 store and return energy as the platform 74 oscillates, leading to forceful oscillations from the relatively small input power of the motor 82 which drives flywheel 70 and eccentric mass 72. The rotating eccentric mass 72 is mounted such that it rotates in a horizontal plane; this allows use of a small motor 82 to rotate flywheel 70 because eccentric mass 72 does not change elevation.

The prime mover of platform 74 may be either the eccentric mass 72 or the springs 80. When the rotating eccentric mass 72 is the prime mover of the system, the amplitude of acceleration of platform 74 is controlled by the speed of rotation of flywheel 70, the radius of displacement of the eccentric mass from the rotational axis 70a of the flywheel, and the mass of the eccentric mass. The mass may be changed by removing or adding weights. Alternatively, the eccentric mass may comprise a bladder which may be selectively emptied or filled with a liquid to vary its mass.

Figure 5:
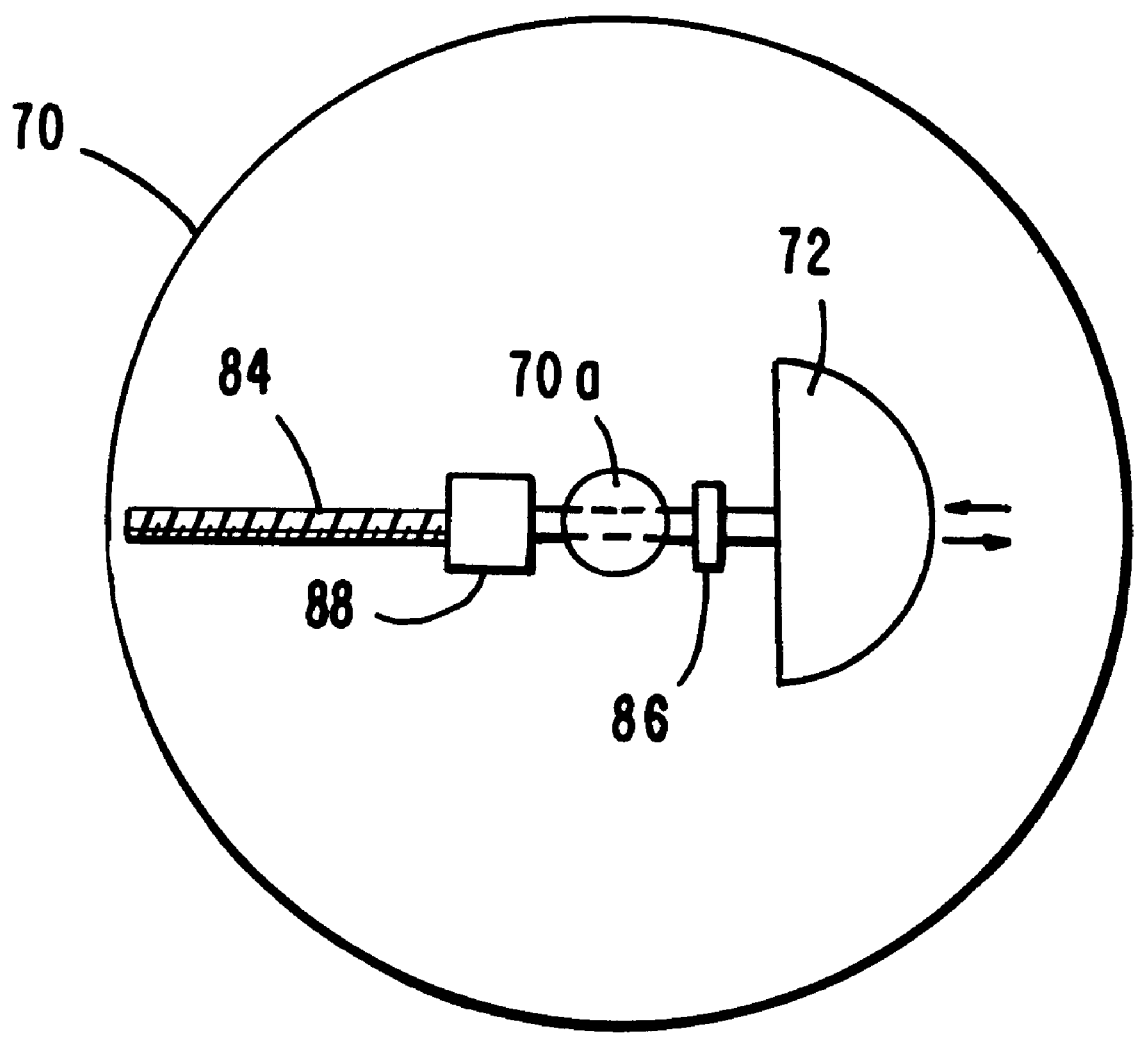
FIG. 5 is a detailed schematic view of an embodiment for adjusting an eccentric weight on the flywheel of FIG. 4.

However, a preferred implementation for varying the amplitude of acceleration accommodates a change in the radius of displacement of the eccentric mass 72 from rotational axis 70a; FIG. 5 shows a mechanism for such an embodiment. The eccentric mass 72 is mounted on a shaft 84 which is held onto the flywheel 70 by first and second bearings 86, 88. The first bearing 86 allows the shaft 84 to slide axially therethrough. The second bearing 88 comprises a releasable locking bearing for holding a position of the shaft 84 connected to eccentric mass 72 when in the locked position and accommodating adjustment of the axial position of shaft 84 in the release position. The second bearing 88 may also comprise a manually adjustable or motor driven adjustment bearing. Shaft 84 may be threaded or comprise teeth for adjustment via a meshed engagement with the second bearing 88. Instead of being connected to a rod, the eccentric mass 72 may be directly connectable to the flywheel 70 at a plurality of different mounting positions, wherein each position defines a different predetermined radial distance from rotational axis 70 a.

The springs 80 may also be sized to be the prime mover of platform 74. In this embodiment the springs 80 provide more force than the eccentric mass 72 during steady state oscillation. Before steady state oscillation is reached, the motor 82 drives the eccentric mass 72 which provides an impulse to begin movement of platform 74. During steady state oscillation, motor 82 provides the energy lost by the springs 80 during each cycle. The force of the springs 80 acting on the eccentric mass 72 determines the frequency of oscillation and amplitude of acceleration. The frequency of oscillation is somewhat adjustable by varying the operating speed of motor 82. However, adjustment of the force provided by springs 80 has the greatest effects on the amplitude of acceleration at a given frequency.

Figure 6A:
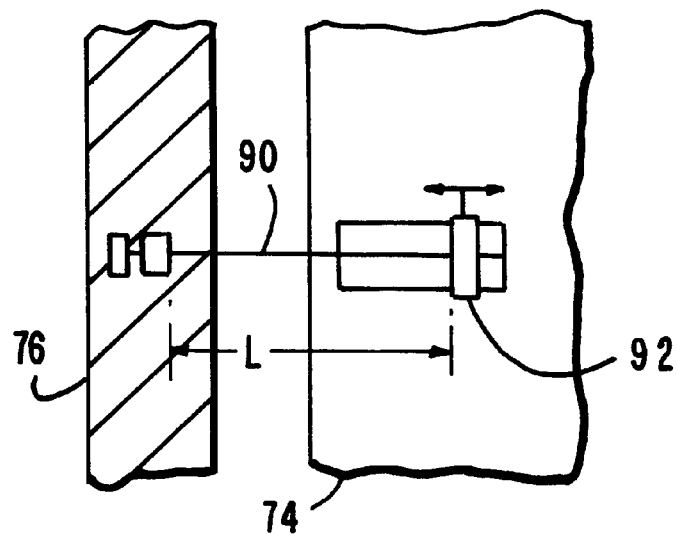
FIGS. 6a and 6b show detailed schematic views of different embodiments of connecting elements arranged between the platform and a stationary frame of FIG. 4.

In lieu of helical springs 80, a rubber band or other similarly resilient element may be employed. As a further alternative, a torsion bar 90 may be used as for example shown in FIG. 6a. When the torsion bar 90 is the prime mover for the platform, the amplitude of acceleration is adjustable by changing the length of torsion bar 90. To accomplish this, one end of torsion bar 90 is fixedly connected to stationary frame 76 and the other end to a sliding element 92. Sliding element 92 is slidable along the axial length of torsion bar 90 to thereby change the active length of the torsion bar and thus effect a change in the spring constant. Alternatively, the torsion bar 90 may be fixedly connected to the sliding element 92 such that torsion bar 90 moves through a bearing connection at the stationary frame 76 for adjusting the active length of the torsion bar.

Figure 6B:
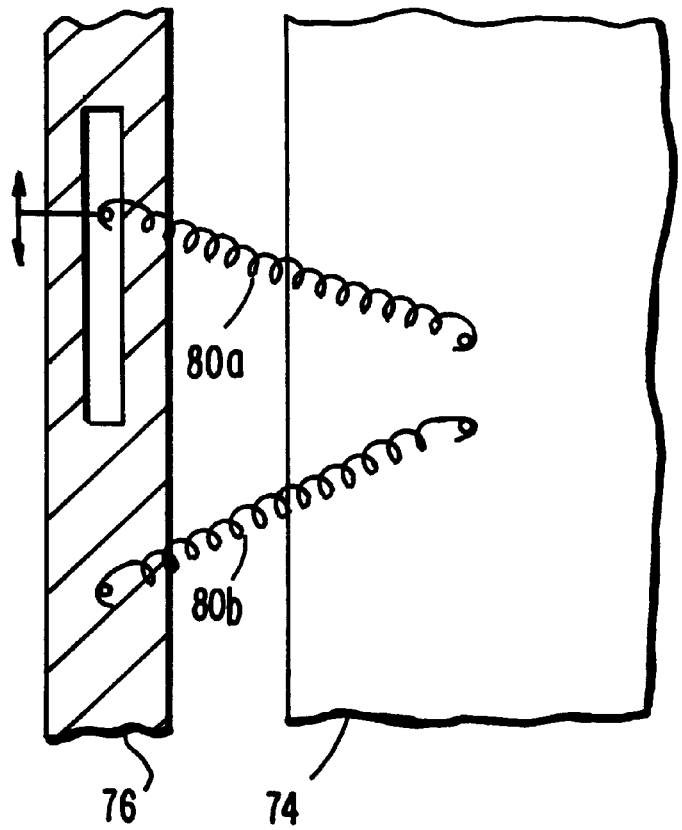

In another embodiment shown in FIG. 6b, two springs 80a and 80b are disposed at one location between platform 74 and stationary frame 76. The spring constant of this system is adjusted for changing the characteristic of oscillation by altering the geometry of the springs 80 a, 80b relative to each other. For example, the angle between the respective extensions of the two springs may be increased or decreased. In addition, preloading of the springs 80a and 80b may be selectively adjusted. In FIG. 6b, the attachment point of spring 80b to stationary frame 76 is adjustable relative to that of spring 80a for changing the geometry of springs 80a and 80b and thereby simultaneously varying the amount of preload. This adjustment affects both the oscillation frequency and the acceleration profile.

Figure 7A:
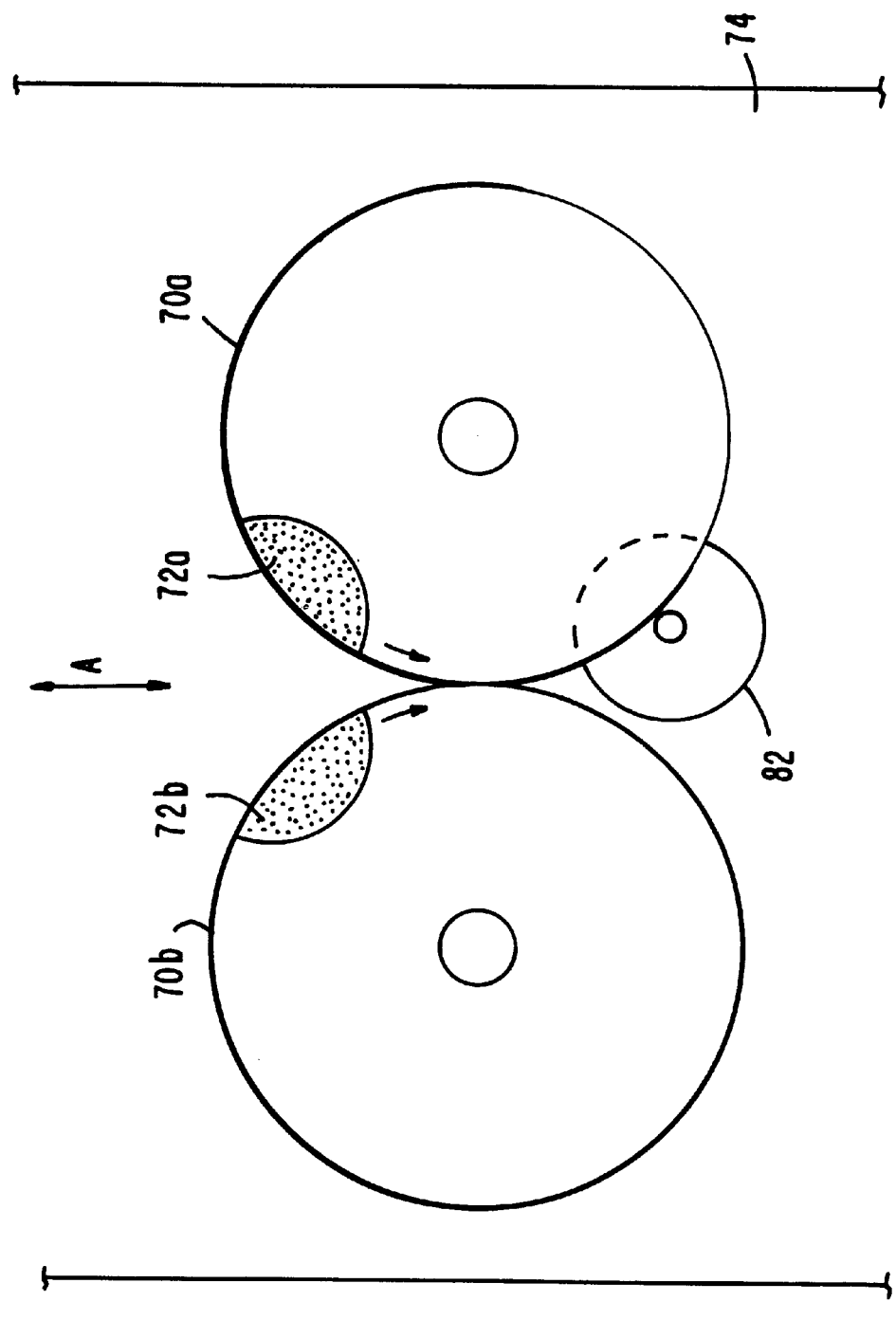
FIG. 7a shows another embodiment of a displacement module of FIG. 4 including two flywheels.

In place of a single flywheel 70, two flywheels 70a and 70b may be employed in another embodiment shown in FIG. 7a. Each flywheel 70a, 70b has a respective eccentric mass 72a, 72b. Masses 72a, 72b are arranged on platform 74 so that the lateral effect of each eccentric mass on platform 74 with respect to the direction of arrow A is cancelled by the other. This arrangement reduces the force that bears against the linear slides 78 and thereby extends the life of the linear slides and/or allows the linear slides to be manufactured of lighter materials and, therefor, less cost. To maintain this lateral motion arrangement, the two flywheels 70a, 70b are positively engaged as, for example, by a meshed engagement. As in the previous embodiments of the flywheel, the eccentric masses 72a and 72b are disposed so that they do not change elevation as they rotate, thereby allowing a small motor 82 to be used to rotate the flywheels.

Figure 7B:
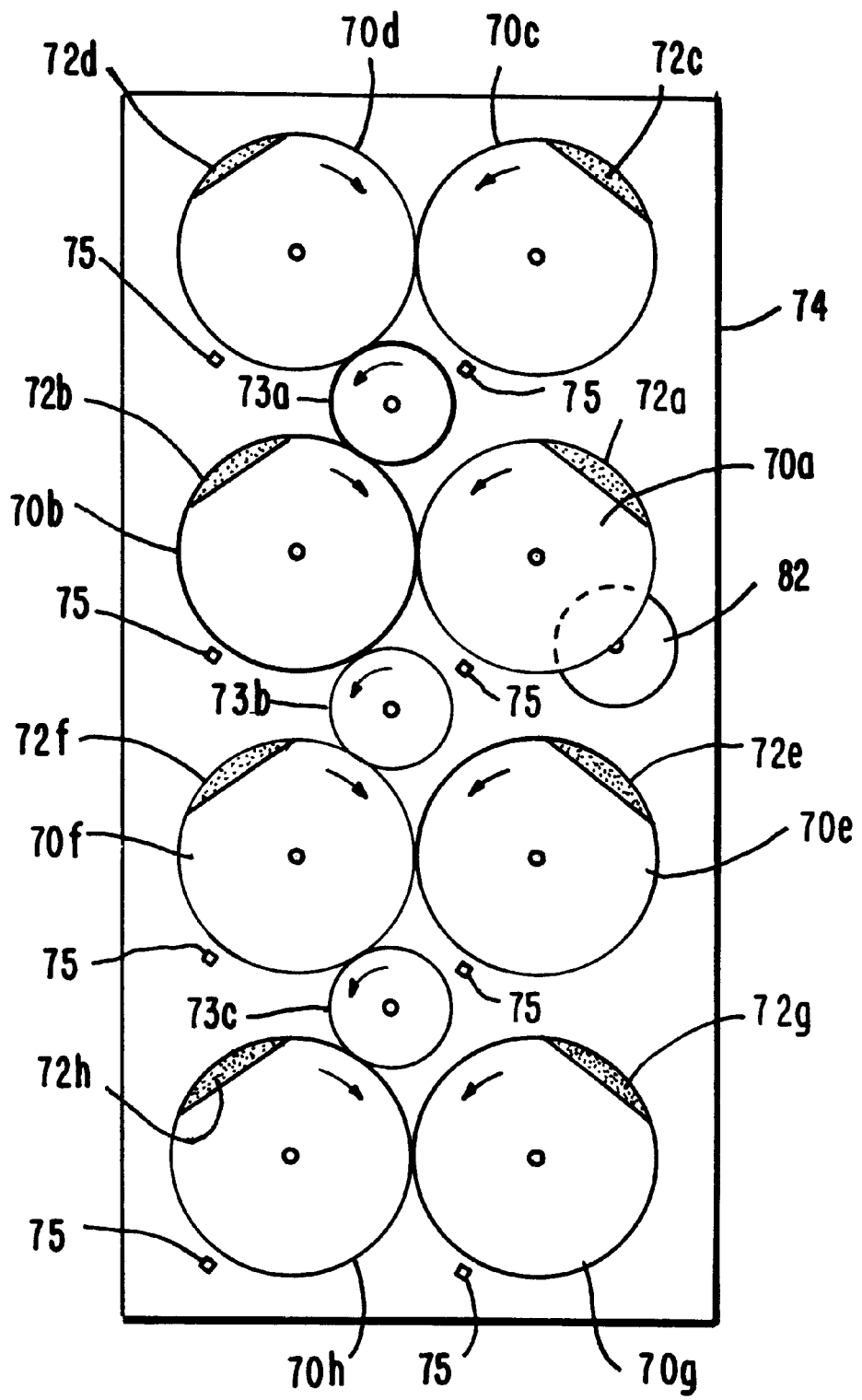
FIG. 7b shows a further embodiment of a displacement module of FIG. 4 including a plurality of flywheels.

The platform 74 is not limited to one or two flywheels. Any number of flywheels may be used. For example, FIG. 7b shows eight flywheels 70a–70h with respective eccentric masse 72a–72h. The eight flywheels 70a–70h are arranged in four pairs, with each pair being arranged for canceling lateral motion. For an adult subject application, each of the eccentric masses 72a–72h weighs approximately 5–20 lbs and rotates at a radius of 4–6 inches from the rotational axis. This embodiment adapts to a form useable with a typical twin size bed. In addition, the plural small masses put less bearing load on the individual bearing for the flywheels 70a–70h than the force that would be applied to one bearing, if the weights were concentrated on one flywheel for producing the same total force.

Also shown in FIG. 7b are connecting wheels 73a, 73b, 73c which are selectively engageable, thereby allowing a selected number of the eccentric masses 72a–72h to rotate via the motor 82. The connecting wheels 73a, 73b, 73c thus allow a variable force to be exerted to the platform without changing speed of the motor 82 or position of the eccentric masses 72a–72h. In a preferred embodiment, the phase relationship between the pairs of flywheels is adjustable such that the net force is continuously adjustable from a minimum value (when the pairs of eccentric masses cancel each other out) to a maximum value (where the pairs of eccentric masses rotation in unison). For example, the connecting wheels 73a, 73b, 73c may comprise a clutch mechanism which allows a controlled slip between the two adjacent pairs of the flywheels 70a–70h it connects. The relative rotational position of the flywheels 70a–70h then determines the net force applied to the platform 74. The relative positions may be determined by position-sensing elements 75. These positioning elements 75 may comprise, for example optical encoders or potentiometers. In the embodiment of FIG. 7b, if connecting element 73b comprises a clutch, the net forces are variable as a sinusoidal function between a maximum force and zero. FIG. 7b depicts all flywheels 70a–70h synchronized which results in maximum force for a given frequency. When the clutch of the connecting element 73b is disengaged, the lower group of flywheels 70e–70h lags behind the upper group of flywheels 70a–70d due to the slip. As the two groups fall further out of synch, the net force decreases until the groups are 180° out of phase, at which point the net force is zero. If the lower group of flywheels is allowed to fall further behind, the net force will increase until the maximum force is again achieved. If the operator does not want to pass through the maximum force state to lower the net force, the rate of rotation of the upper groups of flywheels 70a–70d may be temporarily reduced to reduce the lag between the lower group of flywheels 70e–70h and the upper group of flywheels 70a–70d.

Instead of connecting pairs of flywheels, the connecting wheels 73a, 73b, 73c may be used to connect individual flywheels in embodiments which do not exhibit lateral motion cancellation. The clutch mechanism may be used in this embodiment to allow some flywheels to lag behind the others to alter the net force.

Control of the net force and frequency of the oscillation of the platform 74 may be effected manually through direct adjustments of the motor power and clutch engagement. Alternatively, the control may occur automatically via the processor 20 and in response to the detector 40 of FIG. 8, which is discussed in further detail below.

The characteristics of oscillatory movement of platform 11 in the headward and footward directions, such as the amplitude, frequency and acceleration of motion, are controlled by a processor 20 (see FIG. 1) that transmits control signals to the displacement modules 12 to produce a specific platform motion. Processor 20 may for example comprise a microprocessor system, or an off-the-shelf waveform generator, which interfaces with the available displacement modules 12, such as DC motors. Processor 20 may optionally include means for altering the characteristics of the motion and may include a memory 25 storing motion templates for various types of motions; such means for altering the motion characteristics, and the memory, are described in further detail below.

Referring now to the block diagram of FIG. 8, the processor 20 is signally connected to the displacement module 12, which operatively reciprocates or oscillates the platform 11 as described above. The processor 20 may optionally be connected to an input device 21 such as a keyboard, continuously variable dials, or button presets for altering the frequency, amplitude, acceleration, and/or shape of the waveform of the oscillatory motion. Input device 21 may be embodied in a separate unit from the processor 20 or as an integral part thereof. An optional detector 40 may be utilized as a control device for providing feedback to the processor for correcting its output signals to produce the desired movement of the platform 11. The detector 40 and processor 20 may also be employed as a safety device in which the controller stops the motion of the platform if the detector detects that a characteristic of the motion has exceeded a predetermined limit. Detector 40 may be implemented as an accelerometer, a speedometer, a position detector, or any other type of device that detects the particular characteristics of the motion of platform 11. Although the detector is shown as monitoring the movement of platform 11, it may also be connected for monitoring movement of the subject 30.

In another embodiment, the processor 20 includes or is connected to associated memory 25 that stores one or more templates for producing different types of motions. In this embodiment, the user selects one of the stored templates using the input device 21 and may further adjust the characteristics of the template using the input device 21 to alter the frequency, amplitude, and/or acceleration of platform 11. The memory device 25 may be read only memory or read/write memory in which the user can store his or her own motion templates.

One of the motions of which the platform assembly 10 is capable is a reciprocal motion in the headward and footward directions of the subject 30 at approximately 0.25–1.5 Hz for inducing sleep. Another motion is a mixed frequency motion of 0.25–1.5 Hz; this mixed frequency motion is preferably effected while a subject is asleep on the platform assembly so as to minimize the occurrence of apneas.

Also shown in FIG. 8 is a physiologic monitor 50 for monitoring physiological characteristics of the subject 30. The physiologic monitor 50 and processor 20 may be used to detect adverse cardiorespiratory events, such as central, mixed, and obstructive apneas, prolonged apnea, pulse waveform validated arterial oxygen saturation, heart rate changes from an electrocardiogram, severe hypoxemia, and/or severe bradycardia. Processor 20 is programmed to respond to the detection of an adverse event by rapidly shaking the platform 11 in a non-uniform motion from 2–4 Hz to wake the subject 30 and end the adverse event.

If the adverse event is not terminated by the shaking motion, additional stimulus modules 60 may be activated serially or in parallel with the rapid shaking of the platform 11, depending on the severity of the adverse event. The additional stimulus modules 60 may include visual stimulation such as a strong light source directed at the face of the subject, aural stimulation such as a voice sound calling to the subject to wake up, and a physical stimulation such as a pulsating air column directed onto the skin. Other types of stimuli directly contacting the subject may also be used; however, the preferred method for terminating adverse events is to employ stimuli that do not directly contact the subject because of potential trauma which can be caused by direct contact with the body.

The monitoring device 50 preferably incorporates Respitrace® technology (respiratory inductive plethysmography), electrocardiography, and pulse wave validated pulse oximetry. Instead of Respitrace® technology, monitor 50 may take the form of any type of device for monitoring breathing including other non-invasive, torso placed breathing monitors such as magnetometers, strain gauges, bellows pneumographs, linear displacement transformers, inductive circumferential transducers, and two channel impedance pneumograph as well as devices at the airway such as pneumotachographs or nasal thermistors.

If the subject is an infant, the monitoring device 50 may also detect a crying infant with the processor 20 automatically responding by initiating a rocking motion of the platform 11 to soothe the baby at low, sinusoidal like frequencies from about 0.25–1.5 Hz.

Since motion imparted to the subject's torso by the reciprocating platform 11 will appear as deflections in various physiological waveforms, e.g., respiration, electrocardiogram, electroencephalogram, electromyogram, blood pressure, central venous pressure, thoracocardiograph, etc., it is necessary to filter these deflections from the detected waveforms to allow examination of the primary physiological waveform being monitored if this is of interest to the operator. Filtering may be accomplished by adaptive noise cancellation. A cancellation signal is derived from the detector 40 that records at least one of linear displacement, velocity, and acceleration of the movements of platform 11. An adaptive algorithm in the processor 20 then generates a reference noise signal that comprises an estimate of the noise in the primary signal received at the input of the adaptive filter and subtracts the reference noise signal from the subject-originated signal to provide an accurate estimation of the physiological signal. Electrical noise from the physiological waveforms during oscillation with the motion platform may also be filtered using a computer running software containing high roll-off digital filters to eliminate the oscillatory motion imparted by the platform.

A tracheotomy was performed for measuring volume and providing PEEP of 5 cm $H_2O$. To control for changes in $PaO_2$, which might occur as a result of NIMV, a bias flow of 100% $FiO_2$ was maintained. Baseline values of arterial blood gases were obtained using conventional mechanical ventilation at frequency of 10 breaths per minute, and mean airway pressure of 4.3 cm $H_2O$. After paralysis with pancuronium bromide, the piglets were started on NIMV at frequencies of 4 to 10 HZ. The frequency of reciprocation remained constant during the subsequent 2 hrs. The following table shows the measurements made during the experiments ($*p<0.05$ Bl vs. Time) showing the mean X and the standard deviation (SD) for each measurement:

|  | BI | 5 min | 15 min | 30 min | 60 min | 90 min | 120 min |
| --- | --- | --- | --- | --- | --- | --- | --- |
| pH* | 7.22 (14) | 7.37 (.11) | 7.44 (.09) | 7.48 (.11) | 7.47 (.17) | 7.37 (.11) | 7.38 (0.12) |
| $PaCO_2$* | 55.7 (13) | 31.8 (5.2)* | 27.9 (6.7)* | 25.2 (7.2)* | 28.1 (12.8)* | 31.9 (152)* | 33.2 (17.1)* |
| $PaO_2$* | 284 (122) | 382 (70) | 375 (69) | 378 (64) | 359 (69) | 308 (115) | 323 (134) |
| Mean Blood Press mmHg | 117 (46) | 116 (45) | 116 (48) | 117 (48) | 109 (50) | 109 (46) | 117 (48) |
| Heart Rate beats/min | 151 (45) | 160 (52) | 164 (59) | 146 (27) | 140 (28) | 144 (75) | 130 (9) |

*pH = arterial blood pH, Pa $CO_2$ = arterial pH, $PaCO_2$ = arterial carbon dioxide tension, $PaO_2$ = arterial oxygen tension Movement of platform 11 may also be triggered from the heartbeat of the subject 30 to provide motions within desired portions of the cardiac cycle or from respiration of the subject 30 to provide motions within desired portions of the respiratory cycle. When platform 11 is to be triggered using the heartbeat as the primary signal, monitor 50 may comprise an electrocardiogram or blood pressure monitor. For respiratory system triggering, monitor 50 may comprise an external single or dual band Respitrace® system positioned over the torso or a pneumotachograph air flow sensor located at the airway and mounted on one end of a bias air or oxygen flow system. Feedback loops from the primary physiological signal to the processor 20 implement such triggering controls.

The platform 11 is operable for vibrating at or near the resonance frequency of the subject's respiratory system, such as in the range of about 0.25–15 Hz, to provide assisted ventilation and/or as a sole support of ventilation. The assertion that the platform assembly 10 can provide sole support of ventilation is based upon experiments carried out in anesthetized piglets whose respiratory muscles were paralyzed with intravenous pancuronium.

For the anesthetized piglet experiments, a platform 11 was attached to a displacement module 12 comprising a linear displacement D.C. motor for reciprocally moving the subject 30 to and fro in a horizontal, headward-footward direction, to achieve ventilation without connection to the airways, which is referred to as non-invasive motion ventilation (NIMV) by Nims of Miami Beach, Fla. With significant amplitude of platform movement (i.e. 1.5–2.5 cm) and frequencies of 3–12 Hz, the abdomen of subject 30 moves outward and the ribcage moves inward during one phase of the stroke, and vice versa in the opposite direction of the stroke (see FIGS. 3a & 3b). The experiments utilized anesthetized, paralyzed, normal piglets 3–5 days old and 1.5–2 kg in weight.

A peak to trough airway pressure measured at the proximal end of the tracheotomy ranged from 1.5 to 3.6 cm $H_2O$ during NIMV. The stable normal values of arterial blood gases exhibited during NIMV indicate that the method maintains ventilation without the risk of barotrauma from positive pressure applied to the airway.

Figure 9:
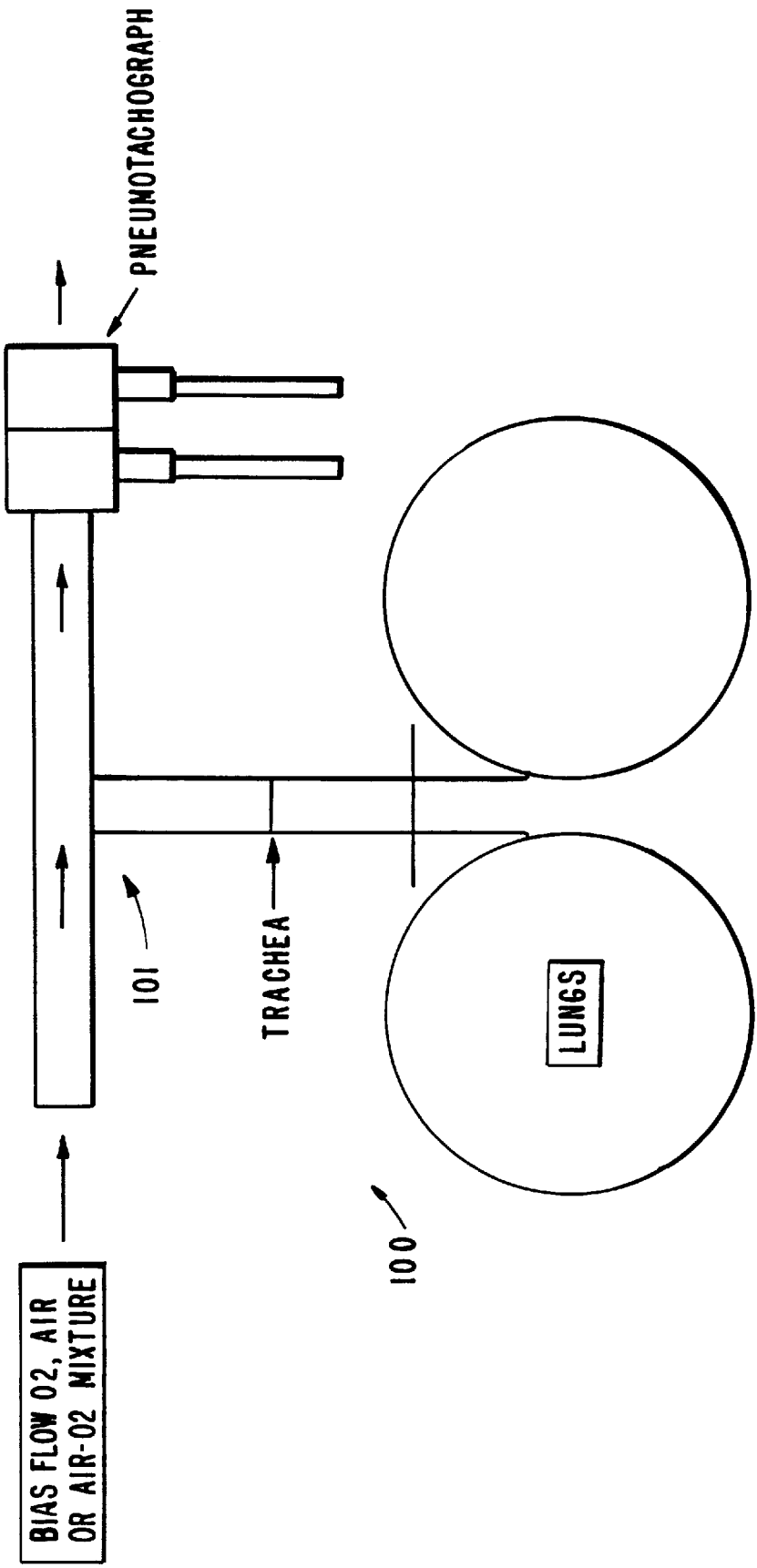
FIG. 9 is a schematic depiction of a connection of the pneumotachograph and the bias flow circuit attached to the airway of the subject through a T-piece during tests of the platform assembly.

The volume per breath caused by each stroke of the platform 11 was determined by integrating the pneumotachograph airflow waveform obtained at the bias flow circuit 100 attached to the airway through a T-piece 101 as shown in FIG. 9. In the preferred embodiment, Continuous Positive Airway Pressure (CPAP) is provided by the bias flow circuit 100 in conjunction with NIMV to stabilize alveoli openings and promote carbon dioxide removal to the atmosphere from the airway opening.

In piglets, the tidal volume (volume of air per breath) at the airway was found to be approximately 75 to 50% of the predicted tidal volume for piglets by weight with the lower values at the higher frequencies of movement (10 Hz) and the higher values at lower frequencies of movement (3 Hz). The amplitude of platform movement was greater with lower frequencies than higher frequencies.

The tidal volumes generated by NIMV using the reciprocating platform 11 are lower than the spontaneous tidal volumes at higher respiratory frequencies than the subject normally breathes. However, these tidal volumes generated by the reciprocating platform 11 enabled adequate ventilation, as confirmed by the measurement of normal values of arterial blood gases, i.e. PaCO2 and PaO2. Furthermore, the pressure required to inflate the lungs using the reciprocating platform 11 is less that for conventional positive pressure mechanical ventilators or positive pressure high frequency oscillatory ventilators. The decrease in required pressure attendant with the reciprocating platform 11 minimizes lung damage that may occur as a consequence of positive pressure inflations with mechanical ventilators, a phenomenon designated "barotrauma" and "volutrauma." Therefore, the anesthetized piglet experiment indicates that the reciprocating platform 11 is an effective ventilatory supportive device.

A further experiment was performed to test the effectiveness of NIMV in the presence of abnormal, stiffened lungs. This was evidenced by satisfactory ventilatory support in three anesthetized, paralyzed piglets in which a suspension of 20% human meconium was instilled into the tracheas. The model for this meconium instilled piglet experiment has its basis in the Meconium Aspiration Syndrome (MAS) which is a common cause of respiratory distress among newborn infants. Approximately 5% of the more than 500,000 meconium-stained babies born in the United States each year develop MAS. One third of these infants develop respiratory failure requiring mechanical ventilation. Neonates with MAS requiring mechanical ventilation have mortality rates of up to 60% and death is often related to a persistent pulmonary hypertension of the newborn that is commonly associated with MAS. Meconium is thought to inactivate endogenous surfactant, the surface active agent lining the pulmonary alveoli.

In the meconium instilled experiment, the three piglets that received intratracheal instillation of meconium exhibited the expected physiological responses, as noted in the medical literature when this agent is administered to anesthetized animals. There was an immediate reduction in respiratory compliance (change of volume divided by change of pressure) signifying increased stiffness of the lungs. Profound hypoxemia also occurred. Cardiac output as reflected from arterial minus mixed venous oxygen content differences decreased. The reciprocating platform 11 using NIMV almost restored PaO2 back to normal levels in one animal at 30 minutes following meconium instillation and at 2 hours in the other two despite failure to increase cardiac output. This phenomenon may relate to regeneration of surfactant and/or a decrease in meconium caused pulmonary arterial hypertension by the high-frequency NIMV. The decrease in pulmonary arterial hypertension resulted from nitric oxide released from the endothelial lining of blood vessels as a result of the increased shear stress due to NIMV induced pulsations in the blood vessels. This improves ventilation to perfusion ratios in the lung which consequently improves arterial oxygenation. In terms of surfactant deficiency, it has been found with several different types of high frequency, positive pressure ventilators that there is significantly less severe histologic alterations than with conventional mechanical ventilation. The decreased severity of atelectasis (collapse of lung tissue), which might be associated with surfactant inactivation, was most striking when compared to animals that were on conventional mechanical ventilators. It may be that high frequency, positive pressure ventilators produced internal vibrations, similar to chest physiotherapy, that mitigated the obstructive nature of meconium. There was also a large volume of normal appearing lung tissue in the animals that received meconium despite not suctioning the tracheobronchial tree to remove it. Finally, the time course of restoration of arterial oxygenation with the reciprocating platform using NIMV was much earlier in time than the timing from reports in the literature using high frequency, positive pressure ventilators.

In addition to high frequency NIMV, the platform 11 may also be utilized for ventilatory support at frequencies near normal breathing rates, which in adults is 12–22 breaths per minute and in newborns is 30–60 breaths per minute. In this application, the reciprocating platform 11 may be used as a sole ventilatory support or for ventilatory assistance to spontaneous breaths in subjects who are breathing with inadequate ventilation. In an embodiment for ventilatory assistance, the movement of platform 11 is triggered when an inspiratory threshold is crossed as measured by monitor 50 from a respiratory waveform or its derivative that originates from the respiratory inductive plethysmograph or a pneumotachograph located at the airway. The augmentation may also be set to trigger on a set time of apnea, at a fixed rate or on a selected fraction of spontaneous breaths, as for example every second breath, every fifth breath, or other intervals or periods.

Platform 11 may also be used at higher frequencies in a vibratory NIMV mode. In this further mode of operation, the reciprocating platform 11 cycles at about 15–40 Hz with strokes of small amplitude, approximately 2–4 mm in length or more and is used for chest wall vibration. Chest wall vibration has two main applications: 1) use in conjunction with tracheal gas insufflation (via a catheter placed within the trachea to deliver oxygen or an air-oxygen mixture), and 2) to alleviate dyspnea (a subject's unpleasant awareness of shortness of breath) in lung disease. The vibratory tidal volumes are in the range of 0.1–0.2 ml per Kg of body weight. For comparison, the high frequency NIMV mode (4–10 Hz) of reciprocating platform 11 described above provides tidal volumes to piglets on the order of 3–5 ml per Kg of body weight. In the vibratory NIMV mode, reciprocating platform 11 provides the same small tidal volumes as the known vibratory plate or disc in any body posture. The reciprocating platform 11 has a maximum vibration frequency of about 40 Hz but distributes the vibratory sensation over the entire torso, a potential advantage over known physiotherapy vibrating discs which are only 25 mm in diameter.

In the first mentioned application of the vibratory NIMV mode, the vibrations aid in diffusion of the gasses in the lungs. In the second application, vibration of the chest wall inspiratory muscles during inspiration (in-phase) reduces breathlessness associated with hypercapnia and resistive loading in normal subjects and patients with chronic obstructive lung disease. Vibration reduces breathlessness because it produces increased neural afferent information from the respiratory system. Application of the vibratory sensation over the entire torso with the platform 11 will greatly influence the afferent information. The vibration during inspiration can be triggered from a monitor 50 such as the Respitrace® plethysmorgraph or pneumotochographic breath waveforms.

The platform 11 may also be fitted with a stationary bicycle so that exercise can be carried out while vibratory NIMV is applied. This arrangement allows patients with chronic lung diseases, such as chronic obstructive lung disease and pulmonary fibrosis, to maintain their physical fitness.

NIMV induced by the reciprocating platform 11 also produces non-ventilatory effects to the lungs. These effects include 1) an increased synthesis in the alveoli and release of surfactant into the airways from the alveoli, 2) an even distribution of pharmacological agents within the lungs, and 3) a clearance of retained bronchopulmonary secretions by means of oscillatory two-phase gas-liquid interaction.

Surfactant, phosphatidylcholine, is a surface active agent synthesized and secreted by alveolar type II cells and constitutes an important component of the alveolar lining fluid. Its classic role is to decrease surface tension in alveolar air spaces to a degree that stabilizes opening of alveolar units, the sites at which gas exchange takes place. Without surfactant, the alveoli would collapse leading to a condition termed atelectasis. In premature infants, deficiency of surfactant occurs because of inadequate synthesis; this leads to infant respiratory distress syndrome, a condition marked by massive pulmonary atelectasis, hyaline membranes within the alveoli, and inflammatory changes. Marked hypoxemia occurs and such patients require mechanical ventilatory support. Treatment consists of prenatal maternal administration of dexamethasone if labor commences during 26–32 weeks after gestation in order to enhance endogenous surfactant synthesis in the fetus. At birth, exogenous surfactant is instilled into the lungs of an infant with this condition. This therapy reduces but does not completely eliminate infant mortality; such patients still often require mechanical ventilation and may develop debilitating or fatal intracranial hemorrhages while on mechanical ventilator therapy. Meconium Aspiration Syndrome, a condition in the newborn that inactivates surfactant, may lead to respiratory distress, hypoxemia and death.

Surfactant is found not only in the alveoli but in bronchioles and small airways. In addition to its role in surface-tension reduction in alveoli, surfactant has several other properties. Any condition in babies or adults that is characterized by mucus abnormality, mucociliary transport deficiency, airways obstruction, or bronchoalveolar collapse could benefit from surfactant therapy; examples of these conditions include, among others, bronchial asthma, pulmonary emphysema, cystic fibrosis, and chronic bronchitis. Further, surfactant has antiinflammatory and bactericidal properties that provide benefits in a variety of lung diseases.

Ventilation enhances movement of surfactant into the airways and hyperpnea (excessive ventilation) increases the activity of cholinephosphate cytidyltransferase, the rate-limiting enzyme in surfactant synthesis. High-frequency NIMV (approximately 0.25–15 Hz) induced with the reciprocating platform 11 has the capability to promote surfactant synthesis and its release from the alveoli into the airways. It can therefore be applied for the treatment of lung diseases marked by surfactant abnormalities as mentioned above.

The even distribution of pharmacological agents within the lungs is also promoted with high frequency NIMV induced with the inventive reciprocating platform 11. This phenomenon is analogous to suspending solid particles in a liquid vehicle by shaking the container. This method could be used in conjunction with medications delivered to the lungs as aerosols, or instilled as liquids, emulsions, or suspensions. Such medications may include among others corticosteroids, antibiotics, bronchodilators, enzymes, antitrypsin, heparin, surfactant, and hormones.

Finally, clearance of bronchopulmonary secretions in the respiratory system is accomplished using high frequency reciprocating motion of the platform 11 by an oscillatory two-phase gas-liquid interaction in the lungs. This is analogous to chest physiotherapy in patients with cystic fibrosis, chronic bronchitis and pneumonia in which the cough is used to propel secretions up the airways. By prolonging the inspiratory phase and shortening the expiratory phase of oscillations, sufficiently high flow rates are developed during expiration to create conditions for transport of secretions by two-phase gas-liquid interaction. The tilting capability of the platform assembly 10 further aids in clearing secretions with the aid of gravity.

In addition to ventilatory effects, the reciprocating platform 11 serves as a device for cardiopulmonary or cardiac support when operated at high respiratory frequencies or normal cardiac frequencies (approximately 0.25–15 Hz). The types of cardiopulmonary or cardiac support include 1) cardiopulmonary resuscitation, 2) counterpulsation, 3) augmentation of cardiac stroke volume, and 4) non-invasive cardiopulmonary bypass. This mode of operation is called Non Invasive Motion (NIM) Cardiopulmonary or Cardiac Support.

With respect to cardiopulmonary resuscitation, operation of the reciprocating platform 11 in the high frequency NIMV mode during a cardiac arrest of subject 30 distorts the chest wall of the subject and thereby actively compresses and decompresses the heart. During a stroke of the reciprocating platform 11 in one direction the chest wall moves outward paradoxically to the abdomen; during a stroke in the opposite direction the chest moves inward paradoxically to the abdomen.

In the experiments discussed above, NIMV supported ventilation in anesthetized paralyzed piglets for at least 2 hours. The platform 11 used in those experiments was also used to achieve CardioPulmonary Resuscitation (NIMCPR). The following describes the results of the NIMCPR experiments.

In these experiments CPR was performed in two tracheotomized, anesthetized, and paralyzed piglets at the end of an experimental protocol using NIMCPR. Two piglets, 1.8 and 2 kg in weight, were placed on a bias flow of 100% $FiO_2$, and PEEP+5 $cmH_2O$. The animals received a lethal dose of KCL, and EKG and blood pressure (BP) measurements confirmed cardiac standstill. The animals remained on NIMCPR at 5 and 10 HZ respectively. NIMCPR was continued for 30 minutes. During that time, the blood gases, pulse pressure difference and mean blood pressure were obtained (see table below). Baseline (BL) measurements on conventional mechanical ventilation (PIP=14, PEEP+2) were done prior to NIMCPR.

| Time | pH | | PaCO2 | | PaO2 | | Pulse Press. Difference | | Mean Blood Pressure | |
|---|---|---|---|---|---|---|---|---|---|---|
| Piglet # | 1 | 2 | 1 | 2 | 1 | 2 | 1 | 2 | 1 | 2 |
| BL | 7.43 | 7.19 | 15.2 | 47.3 | 332 | 345 | 24 | 28 | 88 | 102 |
| 10 m | 7.51 | 7.51 | 8.4 | 10 | 182 | 108 | 12 | 14.3 | 18.5 | 9 |
| 20 m | 7.39 | 7.34 | 12.5 | 19.9 | 124 | 46.5 | 11 | 14 | 18.5 | 9 |
| 30 m | 7.31 | 7.08 | 15.7 | 43.1 | 77 | 45 | 7 | 13.9 | 18.5 | 9 |

Figure 10:
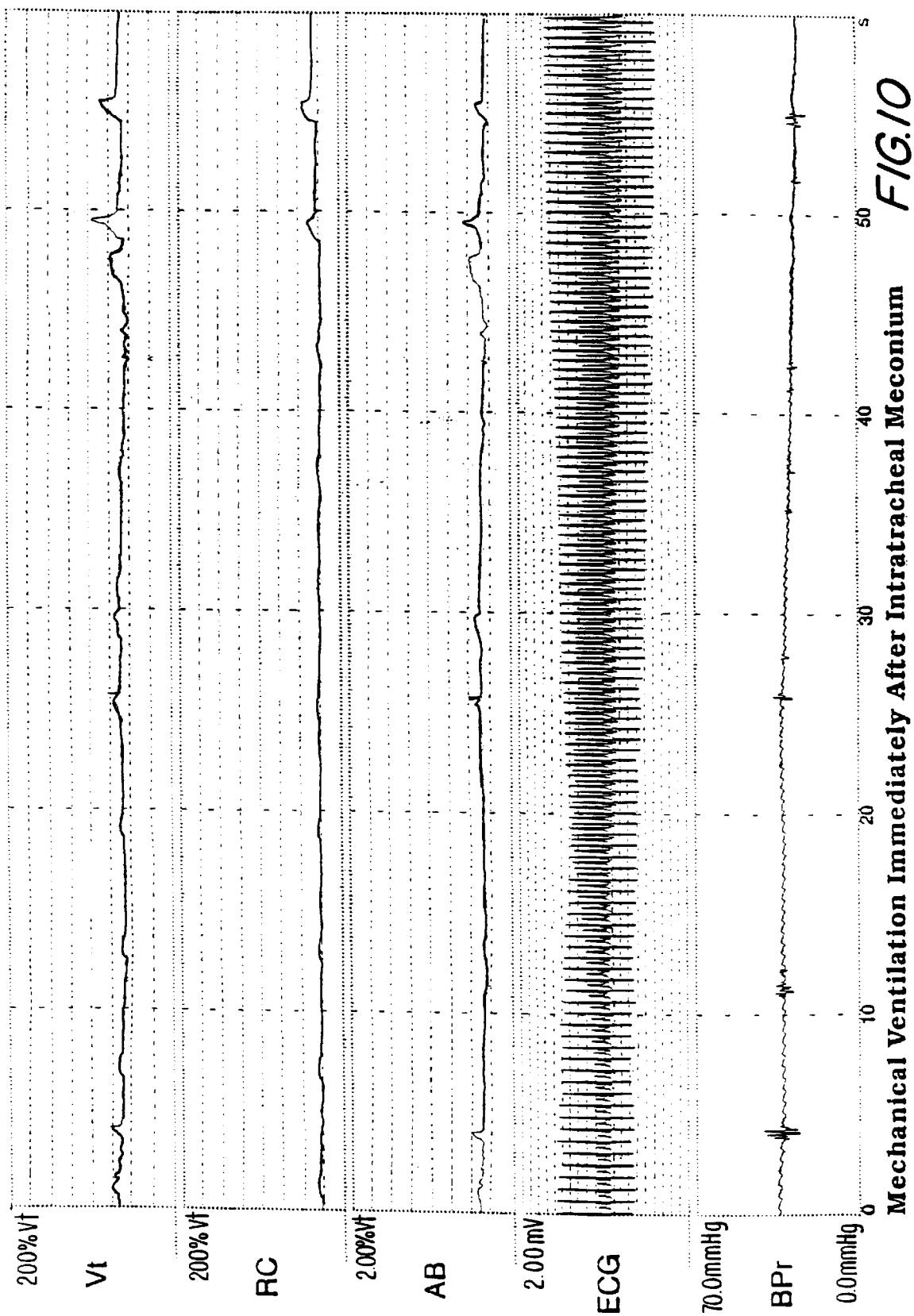
Figure 11:
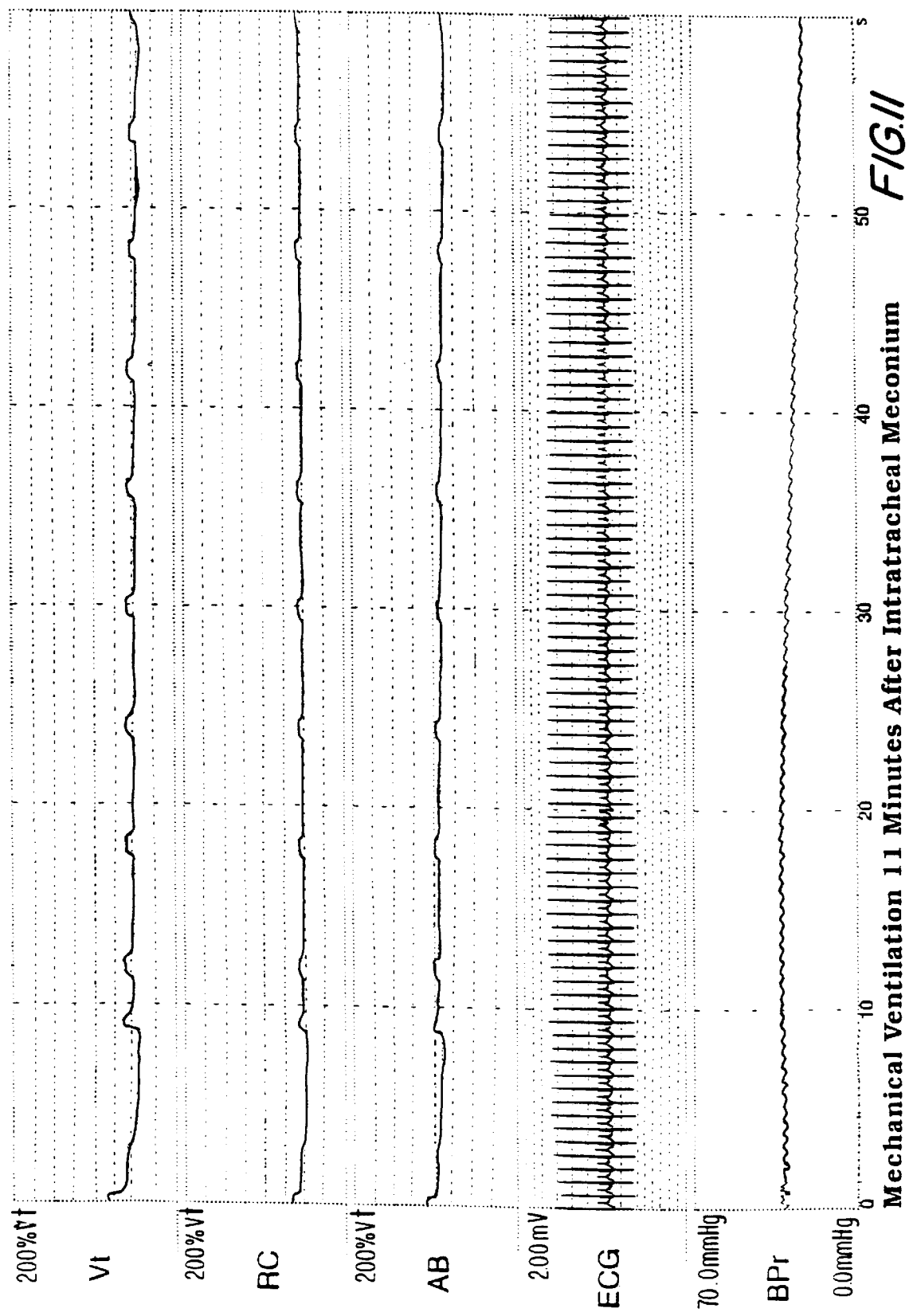
Figure 12:
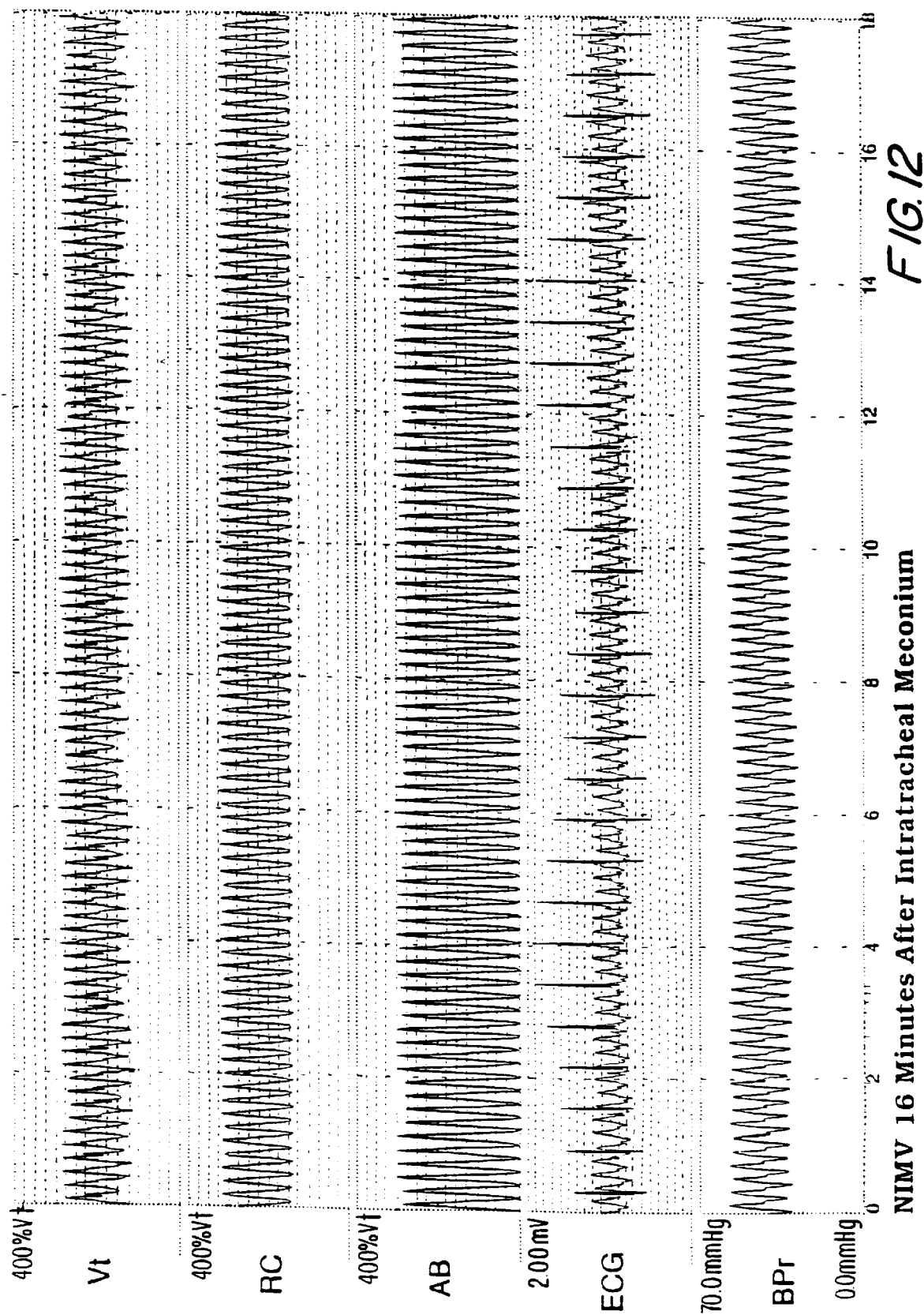

A third animal on NIMV had electromechanical dissociation 10 minutes after intratracheal administration of meconium solution. While NIMV was continued using platform 11, electromechanical dissociation persisted for 18 minutes. (See FIGS. 10 through 19 for recordings of the Tidal volume waveform of Respitrace® (Vt), Rib Cage waveform of Respitrace® (RC), Abdominal waveform of Respitrace® (AB), Electrocardiogram (ECG), and Blood Pressure Waveform (BPr) for the third animal). FIGS. 10 and 11 show a slowing of the heartbeat (ECG) and a fall in the blood pressure (BPr) after meconium instillation. FIGS. 12 and 13 show that NIMS produces rapid oscillations on the respiratory plethysmograph waveforms (Vt, RC, and AB) that are not calibrated to volume because of the multiple degrees of freedom of motion of the respiratory attendant with NIMV. Motion artifacts are also present on the ECG waveform. The heartbeat in FIG. 12 is 10 beats/min, whereas it is less than 0.1 beats/min in FIG. 13. FIG. 14 continues to show profound hypotension and electromechanical dissociation. FIG. 15 shows the higher mean blood pressure with NIMV than without it. Pulsations on the blood pressure waveform are also present. FIGS. 16 and 17 show restoration of an effective mechanical heartbeat and blood pressure after intravenous administration of epinephrine. The favorable action exerted by the epinephrine indicates that blood must have been circulating from the venous to the arterial sides of the circulation, which demonstrates the presence of an effective forward circulation with NIMV. FIG. 17 shows that the mean blood pressure increased from 9 to 249 mmHg for 3 minutes followed by a gradual decline to 160 mmHg for 20 minutes. FIG. 18 shows that NIMCPR produced a phase shift between the chest (RC) and the abdomen (AB) of approximately 180°. Finally, FIG. 19 shows restoration of the electrocardiogram to normal sinus rhythm with a heart rate of approximately 200 beats/min. Thus, these experiments indicate NIMCPR to be a promising method for achieving noninvasive cardiopulmonary resuscitation.

This new method for CPR is effective because the heart valves are opened during cardiac arrest and the blood flows through the heart in a forward direction owing to closure of venous valves at the superior thoracic inlets. The measured mean blood pressure of the piglets was low during NIMCPR but not out of proportion to an adult considering the newborn status of the piglets. Mean blood pressure in adults is about 100 mmHg and, during closed chest compression, is 22–28 mmHg. The normal mean blood pressure of the piglet was about 60 mmHg and during CPR ranged between 9 and 18 mmHg.

The reciprocating platform 11 may operate as a stand-alone system or the processor 20 may be triggered from a monitor 50 such as an electrocardiogram or other pulse monitor to begin operation should cardiac arrest or ventricular fibrillation take place.

External enhanced counterpulsation is another type of cardiac related medical procedure which can be accomplished using the reciprocating platform 11. Similar effects to those observed with conventional counterpulsation are obtained with the reciprocating platform. Here, the monitor 50 comprises an electrocardiogram that is used as a trigger, with the platform 11 moving in a direction such that the chest moves outward to effect increased blood flow during diastole and in the opposite direction during systole to cause systolic unloading. This method of delivering a pulse is designated Non-Invasive Motion Pulse (NIMP).

The effects of yet another procedure, high frequency jet ventilation, may also be obtained with the reciprocating platform 11 triggered by the electrocardiogram to augment cardiac stroke volume using NIMP.

Based upon successful application of NIMCPR for CPR, the reciprocating platform 11 can also be used as a means for non invasive cardiopulmonary bypass to operate on a non-beating heart, in conjunction with mininmally invasive cardiac surgery. Since the motion of platform 11 can be set to a regular periodic motion, robotic control of the operating instruments synchronized to the platform motion will enable a still heart through principles of virtual reality. That is, the heart and the operating instruments would not move relative to each other.

Operation of the reciprocating platform 11 imparts pulsations on blood pressure and flow at the same frequency as the platform. This increases shear stress on the endothelium thereby causing a release of beneficial mediators by the endothelial cells. Among the most important of the mediators is nitric oxide which is the most powerful vasodilator agent produced by the body. The release of these beneficial mediators normally occurs during physical exercise. Therefore, the NIMV using the reciprocating platform 11 may substitute for the beneficial effects of exercise for those who can not exercise because of physical constraints or respiratory difficulties. The nitric oxide which is released as a result of increased endothelial stress, plays a role in the male erection function; thus, utilization of the platform 11 in this manner may also aid impotency.

By cycling various frequencies of the platform 11 in patients who sleep on the system, relief from the restless leg syndrome and painful legs and moving toes syndrome is possible because the movements of the platform simulate limb activity, which is known to relieve these symptoms.

Finally, according to an NIH publication provided by the National Digestive Diseases Information Clearing House on Constipation, lack of exercise can lead to constipation. For example, the publication states that constipation often occurs after an accident or during an illness when one is bedridden and cannot exercise. The reciprocating platform 11 can be operated to shake the abdomen in a manner analogous to or simulative of the up and down movement that takes place with walking and running and, therefore, may similarly promote bowel movements.

Instead of using the various embodiments of displacement modules shown in FIGS. 1, 1a, and 4–7b, a stroller may be pushed back and forth at 0.25–15 Hz to achieve peak acceleration of up to 0.6 g. These forces are effective for ventilating an infant or baby subject. Therefore, ventilation may be performed according to the method of the present invention in locations where specialized platforms with displacement modules are not available. Accordingly, any means effective for attaining peak forces along the z-axis, i.e., along the spine of a subject of up to 0.6 g may be used to provide to assist ventilation, as a source of ventilation and to provide cardiopulmonary or cardiac support.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention is not limited by the embodiments described above which are presented as examples only but can be modified in various ways within the scope of protection defined by the appended patent claims.

We claim:

1. A platform assembly for moving an animal subject in an oscillatory motion, comprising:
   a frame;
   a displacement module having a stationary part fixedly connected to said frame and a movable part operatively movable relative to said stationary part;

a platform having a planar surface for supportably receiving a torso of the subject and connected to said movable part for selected movement of the platform in an oscillatory motion along a line parallel to said planar surface with operative movement of said movable part; and a controller operatively connected to said displacement module for selectively inducing a controlled movement of the movable part at a predetermined frequency, amplitude and acceleration of oscillatory motion of the platform for effecting one of ventilatory assistance to the subject, ventilatory support of the subject, cardiopulmonary/cardiac support of the subject including cardiopulmonary resuscitation and non-invasive cardiopulmonary bypass, and increased endothelial shear stress for releasing beneficial mediators in a vascular system of the subject.

2. The platform assembly of claim 1, wherein said frequency, amplitude and acceleration of oscillatory motion of the platform are further controllable for inducing sleep in the subject.

3. The platform assembly of claim 1, wherein said frequency, amplitude and acceleration of oscillatory motion of the platform are further controllable for minimizing and preventing occurrences of apneas in the subject.

4. The platform assembly of claim 1, further comprising a physiological monitor for monitoring a physiological signal of the subject and signally connected to said controller, and said controller controlling the movement of said platform in response to the physiological signal monitored by the physiological monitor.

5. The platform assembly of claim 4, wherein said physiological monitor is operable for monitoring the subject to detect an adverse event and the controlled movement of the movable part effects on the platform a shaking motion for waking the subject in response to detection of the adverse event.

6. The platform assembly of claim 5, wherein the adverse event comprises one of central, mixed, and obstructive apneas, diminished values of arterial oxygen saturation as measured with pulse waveform validated arterial oxygen saturation, severe hypoxemia, and severe bradycardia.

7. The platform assembly of claim 5, further comprising means for activating an additional stimulatory module in response to detection of the adverse event, wherein said additional stimulatory module comprises one of a strong light source directed at the face of the subject, an auditory stimulator, and a pulsating air column directed on the skin of the subject.

8. The platform assembly of claim 4, wherein said physiological monitor comprises an electrocardiogram and said controlled movement is responsive to the electrocardiogram for providing counterpulsation to the subject.

9. The platform assembly of claim 4, wherein said physiological monitor comprises a device for performing one of respiratory inductive plethysmography, pneumotachography, electrocardiography, and pulse wave validated pulse oximetry.

10. The platform assembly of claim 4, wherein said physiological monitor comprises a breathing monitor from the group consisting of a magnetometer, a strain gauge, a bellows pneumograph, a linear displacement transformer, an inductive circumferential transformer, a two channel impedance pneumograph, a pneumotachograph, and an oronasal thermistor.

11. The platform assembly of claim 4, wherein said physiological monitor operatively monitors at least one physiologic waveform from the group of waveforms comprising respiration, electrocardiogram, electroencephalogram, electromyogram, blood pressure, central venous pressure, and thoracocardiograph.

12. The platform assembly of claim 1, wherein said controlled movement is further controllable for effecting in the subject non-ventilatory effects comprising one of increasing synthesis of alveoli of the subject, evenly distributing pharmacological agents in a respiratory system of the subject, and clearing retained secretions in the respiratory system of a subject.

13. The platform assembly of claim 1, wherein said frequency, amplitude and acceleration of oscillatory motion of the platform are further controllable for treating restless leg syndrome and painful legs and moving toes syndrome of the subject.

14. The platform assembly of claim 1, wherein said controlled movement effects a sinusoidal movement of the platform to cause an outward movement of the subject's abdomen along with an inward movement of the subject's chest in one direction of platform movement and opposite effects on the subject in opposite direction of platform movement for one of assisting and supporting ventilation of the subject.

15. The platform assembly of claim 14, further comprising a continuous positive pressure breathing apparatus with a bias air or oxygen flow operatively connectable to said subject and in a fixed position relative to said frame.

16. The platform assembly of claim 1, wherein said controlled movement is further controllable for effecting on the platform a vibration with a frequency in the range of 30–40 Hz for achieving ventilation of the subject with tracheal gas diffusion.

17. The platform assembly of claim 1, wherein said controlled movement is further controllable for effecting on the platform vibrations with a frequency in the range of 30–40 Hz for reducing perception of breathlessness of the subject for a subject having a lung disease.

18. The platform assembly of claim 1, wherein said controlled movement is further controllable for effecting a movement of the platform that causes outward movement of an abdomen of the subject and inward movement of a chest of the subject in one direction of platform movement and an opposite effect in opposite direction of platform movement for cardiopulmonary resuscitation of the subject when a heart of the subject has arrested or experienced ventricular fibrillation.

19. The platform assembly of claim 18, further comprising a continuous positive pressure breathing apparatus with a bias air or oxygen flow operatively connectable to said subject and in a fixed position relative to said frame.

20. The platform assembly of claim 1, wherein said controlled movement effects on the platform a movement which effects paradoxical movement of an abdomen and chest of the subject for increasing motility of intestines of the subject.

21. The platform assembly of claim 1, wherein said displacement module comprises one of an electric solenoid, a pneumatic solenoid, an electric motor with a linear shaft, a hydraulic actuator, and a flywheel.

22. The platform assembly of claim 1, further comprising a detector for detecting one of a position, speed, and acceleration of the platform and transmitting an output signal to said controller.

23. The platform assembly of claim 22, further comprising means for detecting physiological waveforms of the subject and means for filtering deflections in the physiological waveforms of the subject caused by the motion of the platform assembly.

24. The platform assembly of claim 23, wherein said means for filtering deflections consists of one of an adaptive noise cancellation filter receiving the output signal transmitted from said detector and a digital filter in a computer.

25. The platform assembly of claim 1, further comprising an input device operatively connected to said controller for adjusting one of the frequency, amplitude and acceleration of the motion of said platform.

26. The platform assembly of claim 25, further comprising a memory connected to said controller and storing a plurality of templates for inducing selected controlled movements of said movable part for effecting different types of predetermined motion of the platform, wherein the input device is operable for selecting among the plural templates.

27. The platform assembly of claim 1, wherein the platform is tiltable relative to the frame so as to elevate one of the feet and head of the subject relative to the other.

28. The platform assembly of claim 1, wherein the platform comprises a first part and a second part; and wherein said first part is tiltable relative to the second part for elevating one of the feet and head of the subject relative to the other.

29. The platform assembly of claim 1, wherein said predetermined frequency is within a range of about 0.25 to 15 Hz and said amplitude is within a range of about 1.5 to 2.5 cm.

30. The platform assembly of claim 29, wherein said displacement module is operatively connected to opposite ends of said platform so that said displacement module operatively pushes and pulls said platform with operative movement of said movable part.

31. The platform assembly of claim 1, wherein said frame comprises a conventional bed frame and said platform is arranged for supportedly receiving a mattress so that the mattress lies intermediate said platform and the subject.

32. The platform assembly of claim 1, wherein said displacement module is operatively connected to opposite ends of said platform so that said displacement module operatively pushes and pulls said platform with operative movement of said movable part.

33. An operatively oscillating platform assembly, comprising:
- a platform having a surface for supportably receiving a torso of an animal subject;
- means for operatively moving the platform through an oscillatory motion;
- a monitor operatively connectable to the subject for monitoring a physiological characteristic of the subject and outputting a monitor signal in response to the physiological characteristic; and
- a controller for receiving said monitor signal and operatively connected to said means for moving for controlling one of a frequency and a speed of oscillatory motion of the platform in response to said monitor signal.

34. The oscillating platform assembly of claim 33, wherein said moving means is operable for moving the platform through an oscillatory motion having a predetermined frequency and speed selected for one of assisting ventilation of the subject, supporting ventilation of the subject, and providing cardiopulmonary/cardiac support for the subject.

35. The oscillating platform assembly of claim 34, wherein the cardiopulmonary/cardiac support comprises one of cardiopulmonary resuscitation and non-invasive cardiopulmonary bypass, and increased endothelial shear stress in the vascular system to cause release of beneficial mediators.

36. The oscillating platform assembly of claim 34, wherein said oscillatory motion comprises a frequency within a range of about 0.25 to 15 Hz and an amplitude within a range of about 1.5 to 2.5 cm.

37. The oscillating platform assembly of claim 33, wherein said oscillatory motion comprises one of a high-frequency oscillatory motion, a low-frequency oscillatory motion, and a vibratory motion.

38. An operatively oscillating platform assembly for moving an animal subject in an oscillatory motion, comprising:
- a frame;
- a platform having a substantially planar surface for receiving in supported relation the animal subject, said platform being movably mounted on said frame for movement relative to said frame along a line parallel to said substantially planar surface; and
- a displacement module connected to said platform for effecting an oscillatory motion of said platform along said line, said displacement module comprising a flywheel rotatably mounted to said platform, a weight eccentrically mounted to said flywheel, means for rotating said flywheel, and means connected to one of said flywheel, said weight and said frame for controlling at least one of a frequency, amplitude and acceleration of said oscillatory motion.

39. The platform assembly of claim 38, wherein said means for controlling comprises means for adjusting a mass of said eccentric weight.

40. The platform assembly of claim 38, wherein said means for controlling comprises means for adjusting a position of said eccentric weight relative to an axis of rotation of said flywheel.

41. The platform assembly of claim 38, wherein said means for controlling comprises means for adjusting a rate of rotation of said flywheel.

42. The platform assembly of claim 38, further comprising a resilient connector connected between said platform and said frame for allowing movement of said platform relative to said frame during rotation of said flywheel and for holding said platform at a default position with respect to said frame when said flywheel is not rotating.

43. The platform assembly of claim 42, wherein said resilient connector comprises a spring and said means for controlling comprises means for adjusting a tension of said spring.

44. The platform assembly of claim 42, wherein said resilient connector comprises first and second springs and said means for controlling comprises means for adjusting a relative geometry of said first and second springs and means for adjusting a tension of at least one of said first and second springs.

45. The platform assembly of claim 42, wherein a first force transmitted to said platform along said direction of oscillatory motion by said eccentric mass is greater than a second force transmitted to said platform along said direction of oscillatory motion by said resilient connector during steady state oscillatory motion such that said eccentric mass is a prime mover of said platform during steady state motion of the platform relative to said frame.

46. The platform assembly of claim 42, wherein a first force transmitted to said platform along said direction of oscillatory motion by said eccentric mass is less than a second force transmitted to said platform along said direction of oscillatory motion by said resilient connector during steady state oscillatory motion such that said resilient connector is a prime mover of said platform during steady state oscillatory motion of the platform relative to said frame.

47. The platform assembly of claim 38, wherein said oscillatory motion defined by a frequency within a range of about 0.25 to 15 Hz and a peak acceleration within a range of about ±0.25 g to ±1.5 g.

48. The platform assembly of claim 38, wherein said means for controlling comprises means for effecting one of ventilatory assistance to the subject, ventilatory support of the subject, cardiopulmonary/cardiac support of the subject, and increased endothelial shear stress for releasing beneficial mediators in a vascular system of the subject.

49. The platform assembly of claim 38, wherein said frame comprises a bed frame and said platform is arranged for supportedly receiving a mattress of said bed frame such that said mattress lies intermediate said platform and the animal subject.

50. The platform assembly of claim 38, wherein said means for controlling said oscillatory motion comprises means for effecting a movement of the platform that causes outward movement of an abdomen of the animal subject and inward movement of a chest of the subject in one direction of platform movement and an opposite effect in an opposite direction of platform movement for effecting one of ventilatory assistance to the subject, ventilatory support of the subject, cardiopulmonary/cardiac support of the subject, and increased endothelial shear stress for releasing beneficial mediators in a vascular system of the subject.

51. The platform assembly of claim 38, wherein said flywheel of said displacement module comprises first and second flywheels rotatably mounted to said platform and first and second weights eccentrically mounted to respective ones of said first and second flywheels, said first and second weights arranged such that each said first and second weights cancel lateral motion of the other during rotation.

52. The platform assembly of claim 51, wherein said first flywheel is connectable to said second flywheel via said connecting wheel at variable relative position for adjusting a total net force exerted on said platform.

53. The platform assembly of claim 51, wherein said connecting wheel comprises a clutch mechanism for controlling an amount of slip between said first and second flywheels.

54. The platform assembly of claim 51, wherein each said first and second flywheels comprises a pair of flywheels having weights eccentrically mounted thereon, each of said weights arranged for canceling lateral motion of the other of said weights of said pair of flywheels.

55. The platform assembly of claim 38, wherein said flywheel of said displacement module comprises first and second flywheels rotatably mounted to said platform and first and second weights eccentrically mounted to respective ones of said first and second flywheels, said means for rotating said flywheel comprising means for rotating said first flywheel, said platform assembly further comprising a connecting wheel for selectively connecting said first flywheel to said second flywheel.

56. A method for providing support or assistance to one of a cardiorespiratory function and a cardiovascular function of a living subject, comprising the steps of:
positioning and holding the living subject on a movable platform so that at least a torso of the living subject is movable in response to a movement of the movable platform;
initiating a reciprocating motion of the movable platform substantially along a headward and footward direction with respect to the living subject;
controlling a characteristic of the reciprocating motion of the platform including one of a frequency, an amplitude, and an acceleration of the motion of the movable platform with a controller so that the reciprocating motion provides support or assistance to the one of a cardiorespiratory function and a cardiovascular function of the living subject.

57. The method of claim 56, wherein said step of controlling further comprises controlling said characteristic of the reciprocating motion to induce a paradoxical movement of a chest and an abdomen of the subject in response to the reciprocating motion.

58. The method of claim 56, wherein said step of controlling a characteristic comprises manually adjusting the controller.

59. The method of claim 58, further comprising the step of recording the characteristics of the manually adjusted reciprocating motion to a memory in the controller.

60. The method of claim 56, wherein said step of controlling a characteristic comprises detecting the characteristic of the motion of the platform using a detector, transmitting a detected signal representing the detected motion to the controller, and controlling the platform in response to the detected signal.

61. The method of claim 60, wherein said step of controlling further comprises terminating the reciprocating motion if the signal representing the detected motion exceeds a predetermined threshold.

62. The method of claim 56, further comprising the step of monitoring a physiologic sign of the living subject.

63. The method of claim 62, wherein the step of monitoring a physiologic sign comprises using an adaptive noise cancellation filter to filter deflections caused by the reciprocating motion.

64. The method of claim 62, wherein said step of initiating the reciprocating motion further comprises initiating the reciprocating motion in response to an adverse cardiorespiratory or cardiovascular event detected during said step of monitoring a physiologic sign.

65. The method of claim 64, wherein said step of controlling a characteristic of the reciprocating motion of the platform further comprises controlling the reciprocating motion to wake the living subject for terminating the detected adverse cardiorespiratory or cardiovascular event.

66. The method of claim 62, wherein said step of controlling a characteristic of the reciprocating motion comprises controlling the reciprocating motion in response to the physiologic sign.

67. The method of claim 56, wherein said step of controlling a characteristic of the reciprocating motion of the platform further comprises controlling the characteristic of the reciprocating motion for assisting or supporting ventilation of the living subject.

68. The method of claim 56, wherein said step of controlling a characteristic of the reciprocating motion of the platform further comprises controlling the characteristic of the reciprocating motion for assisting tracheal gas insufflation in the subject.

69. The method of claim 56, wherein said step of controlling a characteristic of the reciprocating motion of the platform further comprises controlling the characteristic of the reciprocating motion for alleviating dyspnea in the subject.

70. The method of claim 56 wherein said step of controlling a characteristic of the reciprocating motion of the platform further comprises controlling the characteristic of the reciprocating motion for administering cardiopulmonary resuscitation of the living subject.

71. The method of claim 56, wherein said step of controlling a characteristic of the reciprocating motion of the platform further comprises controlling the characteristic of the reciprocating motion for providing non-invasive cardiopulmonary bypass.

72. The method of claim 56, further comprising the step of monitoring a heart rhythm of the living subject with an electrocardiogram and wherein said step of controlling a characteristic of the reciprocating motion of the platform further comprises controlling the characteristic of the reciprocating motion in response to the electrocardiogram for augmenting cardiac stroke volume.

73. The method of claim 56, further comprising the step of monitoring a heart rhythm of the living subject with an electrocardiogram and wherein said step of controlling a characteristic of the reciprocating motion of the platform further comprises controlling the characteristic of the reciprocating motion in response to the electrocardiogram for increasing blood flow in the living subject.

74. The method of claim 56, wherein said step of controlling a characteristic of the reciprocating motion of the platform further comprises controlling the characteristic of the reciprocating motion for producing endothelial stress.

75. The method of claim 56, wherein said step of controlling a characteristic of the reciprocating motion of the platform further comprises controlling the characteristic of the reciprocating motion for increasing the motility of intestines of the living subject.

76. The method of claim 56, wherein said step of controlling a characteristic of the reciprocating motion includes adjusting a frequency within a range of frequencies including 0.25 to 15 Hz.

77. The method of claim 56, within said step of controlling a characteristic of the reciprocating motion includes adjusting an amplitude within a range of amplitudes including 1.5 to 2.5 cm.

78. The method of claim 56, wherein said step of controlling a characteristic of the reciprocating motion includes adjusting a peak accleration of the motion within a range of accelerations including ±0.25 g to ±1.5 g.

* * * * *